(12) United States Patent
Bowman et al.

(10) Patent No.: US 10,299,719 B2
(45) Date of Patent: May 28, 2019

(54) SYSTEMS AND METHODS FOR ESTABLISHING THE STIFFNESS OF A BONE USING MECHANICAL RESPONSE TISSUE ANALYSIS

(71) Applicant: OHIO UNIVERSITY, Athens, OH (US)

(72) Inventors: Lyn Bowman, Athens, OH (US); Patricia A. Arnold, Athens, OH (US); Emily R. Ellerbrock, Athens, OH (US)

(73) Assignee: Ohio University, Athens, OH (US)

( * ) Notice: Subject to any disclaimer, the term of this patent is extended or adjusted under 35 U.S.C. 154(b) by 711 days.

(21) Appl. No.: 14/782,712

(22) PCT Filed: Apr. 11, 2014

(86) PCT No.: PCT/US2014/033816
§ 371 (c)(1),
(2) Date: Oct. 6, 2015

(87) PCT Pub. No.: WO2014/169217
PCT Pub. Date: Oct. 16, 2014

(65) Prior Publication Data
US 2016/0058365 A1    Mar. 3, 2016

Related U.S. Application Data

(60) Provisional application No. 61/811,037, filed on Apr. 11, 2013.

(51) Int. Cl.
*A61B 5/00* (2006.01)

(52) U.S. Cl.
CPC .......... *A61B 5/4509* (2013.01); *A61B 5/0051* (2013.01); *A61B 5/442* (2013.01);
(Continued)

(58) Field of Classification Search
CPC .......................... A61B 5/4509; A61B 5/0051
See application file for complete search history.

(56) References Cited

U.S. PATENT DOCUMENTS

| 5,006,984 A | 4/1991 | Steele |
| 5,487,395 A | 1/1996 | Strowe |
| 7,485,100 B2 | 2/2009 | Garcia-Webb et al. |

FOREIGN PATENT DOCUMENTS

WO    2012/089221 A1    7/2012

OTHER PUBLICATIONS

Cotton, Jr et al. "Ulna Simulation Assesses Sensitivity to Bone Elastic Modulus Variations in a MRTA test". Abstract presented at 2012 American Society of Biomechanics 36th Annual Meeting from Wednesday, Aug. 15, 2012 to Saturday, Aug. 18, 2012. Abstract saved online at http://www.asbweb.org/conferences/2012/topics/index.html between Oct. 5, 2012 and Nov. 5, 2012; pp. 231-232.

(Continued)

*Primary Examiner* — Daniel L Cerioni
*Assistant Examiner* — Yasmeen S Warsi
(74) *Attorney, Agent, or Firm* — Dinsmore & Shohl LLP

(57) ABSTRACT

Parametric model based computer implemented methods for determining the stiffness of a bone, systems for estimating the stiffness of a bone in vivo, and methods for determining the stiffness of a bone. The computer implemented methods include determining a complex compliance frequency response function Y(f) and an associated complex stiffness frequency response function H(f) and fitting a parametric mathematical model to Y(f) and to H(f). The systems include a device for measuring the stiffness of the bone in vivo and a data analyzer to determine a complex compliance frequency response function Y(f) and an associated complex stiffness frequency response function H(f). The methods for determining the stiffness include fitting a parametric model to stiffness of the skin-bone complex as a function of frequency H(f) and the compliance of the skin-bone complex as a function of frequency Y(f).

28 Claims, 6 Drawing Sheets

(52) U.S. Cl.
CPC .......... *A61B 5/4504* (2013.01); *A61B 5/6824* (2013.01); *A61B 5/6831* (2013.01); *A61B 5/7242* (2013.01); *A61B 5/7246* (2013.01); *A61B 5/7253* (2013.01); *A61B 5/7278* (2013.01); *A61B 2560/0475* (2013.01); *A61B 2562/0219* (2013.01); *A61B 2562/0252* (2013.01); *A61B 2562/14* (2013.01)

(56) References Cited

OTHER PUBLICATIONS

"MIT and Ohio University Use Vibration in Research", The Modal Shop, Inc, News and Events, Jan. 9, 2013, www.modalshop.com/news.asp?P=MIT_And_Ohio_University_Use_Vibration_in_Research&NID=137.
International Search Report for PCT/US2014/033816 dated Nov. 13, 2014.
International Preliminary Report for PCT/US2014/033816 dated Oct. 22, 2015.
European Office Action for 14783154.9 dated Nov. 27, 2015.
Altenburger et al., "Mathematical Modeling of Skin-Bone Systems in Mechanical Response Tissue Analysis", Ohio University Student Expo 2011, May 13, 2011.
Charlton et al., "Accuracy of Mechanical Response Tissue Analysis (MRTA) Measurements on an Artificial Human Ulna", Ohio University Student Expo 2011, May 13, 2011.
Van Horne et al., "Precision of Mechanical Response Tissue Analysis (MRTA) Measurements", Ohio University Student Expo 2011, May 13, 2011.

SYSTEMS AND METHODS FOR ESTABLISHING THE STIFFNESS OF A BONE USING MECHANICAL RESPONSE TISSUE ANALYSIS

CROSS REFERENCE TO RELATED APPLICATIONS

This application is a 35 U.S.C. § 371 national state entry of International Application No. PCT/US2014/033816, filed Apr. 11, 2014 which claims priority to U.S. Provisional Patent Application No. 61/811,037, filed Apr. 11, 2013, the teachings of which are incorporated by reference herein in their entirety.

FIELD

This application generally relates to in-vivo determination of bone stiffness. Specifically, this application relates to systems and methods for establishing the stiffness of a bone using mechanical response tissue analysis (MRTA).

BACKGROUND

Bone health affects the overall health and quality of life of people around the world; for example, over 1.5 million older Americans suffer fractures due to weak bones each year. The bony skeleton provides support, mobility, and protection to the body, and serves as a storage area for essential minerals such as calcium, phosphorus and magnesium. Bone is a composite material made up of protein, minerals, and living bone cells. Collagen protein serves as the framework of the bone and provides resilience and ductility. The minerals, in the form of crystals dispersed around and between collagen fibers, stiffen the bone's protein structure.

There are two types of bone: cortical (compact) and cancellous (trabecular). Cortical bone is configured for support and protection and is arranged as densely packed parallel collagen fibrils organized in layers. This dense cortical bone is located, for example, in the shafts (diaphyses) of the long and short bones of the extremities. Cancellous (trabecular) bone is a porous type of bone located, for example, at the ends (epiphyses) of long bones and in the vertebrae. Cancellous bone provides strength without adding much weight, as it is configured to transfer stresses to the stronger, more massive cortical bone.

Bone is a living tissue that is constantly turning over and regenerating throughout its lifespan. Old bone is broken down (resorbed), creating a void, and new bone is formed in the void. Under normal conditions there is a continuous cyclic remodeling of bone, where osteoclasts remove old and micro damaged bone by acidification and proteolytic digestion, and osteoblasts secrete collagen and other specialized matrix proteins to synthesize new bone. Many hormones, including vitamin D, parathyroid hormone, calcitonin, estrogen, and testosterone, are involved in the regulation and complex interaction between the skeleton, intestine, and kidneys to maintain mineral homeostasis in the body (bones). Overall bone health largely relies on the proper balance of such hormones. Additionally, adequate nutrition and high impact physical activity are contributors to adequate bone health. During childhood and through the teenage years, normal healthy bones experience more bone formation than resorption. However, as humans age, increased bone resorption, decreased bone formation, or a combination of both, lead to a weakening of bones as the net result is less bone formation than resorption.

Further, bone diseases may disrupt normal bone functioning and can make bones weak. One common bone disease is osteoporosis. Osteoporosis is a skeletal disorder characterized by decreased bone strength predisposing to an increased risk of fracture. There are two types of osteoporosis: (1) Type 1 osteoporosis is characterized by a rapid loss of cancellous bone and a small loss of cortical bone in the hips, spine, and wrists of postmenopausal women; and (2) Type 2 (senile) osteoporosis affects both elderly men and women and, is characterized by a loss of cortical and cancellous bone in predominantly cortical bone sites, which is where a majority of non-vertebral fractures after the age of 60 occur in both men and women.

The strength of bone depends on the quality of the bone including the architecture, turnover, damage accumulation, and mineralization of the bone. Bone mineral density (BMD) describes the amount of mineral per area measured and is believed to account for only approximately 70% of bone strength. Current techniques used to diagnose osteoporosis and identify fracture risk focus primarily on measuring bone mineral density. One such technique of measuring BMD is Dual X-ray absorptiometry (DXA). DXA noninvasively measures the transmission of x-rays with high and low energy photons through the body. A DXA measurement represents the sum of cortical and trabecular bone within the bone area scanned as part of the procedure. The results of a DXA scan are presented as a Z score and a T score, where the Z score is the number of standard deviations the measured result is from the mean for age and sex and the T score compares the measured BMD result with the average BMD of healthy young adults.

Other such techniques used to measure BMD include peripheral quantitative computed tomography (pQCT) and high resolution peripheral quantitative computed tomography (HRpQCT), in which 2-dimensional DxA images are made from many different angles around the body or limb and processed by a computer to create a 3-dimensional representation of a body part. These 3-dimensional measurements of bone density and structure can be used as inputs for finite element analyses of bone stiffness and strength.

However, such techniques of measuring BMD are limited in that they are not capable of providing direct insight into the mechanical properties of the bone. For example, changes in the mechanical properties of the bone can increase fracture risk while leaving bone mineral density intact, thus remaining undetected by such conventional screening methods.

Techniques for direct biomechanical testing of bone have also been developed. Direct biomechanical testing of bone is desired in that it provides information about mechanical integrity of bone. Currently, quasistatic mechanical testing (QMT) is the gold standard for directly measuring the strength of materials, including bone. QMT measures the force, which is applied at a very slow speed and corresponds to a constant strain rate, versus displacement. QMT can be utilized in the performance of many differing types of mechanical tests such as, e.g., 3-point bending. To perform 3-point bending, or flexure tests, the specimen (bone) is supported at each end, and a force is applied at the midspan, where the sensitivity is greatest to elastic modulus. As the bone bends, fibers near the top surface undergo compressive forces and the fibers near the lower surface experience tensile forces.

Bone bending strength represents the maximum bending force a bone can bear before it breaks. Bone strength is measured with QMT as the peak force prior to fracture in a bending test, which occurs in the plastic region of the bone. The plastic region being the area under a force-displacement curve where permanent damage is accumulating within the bone, whereas the elastic region represents the area under a force-displacement curve where no permanent damage is being done and the bone will return to its original shape when the force is released. Bone bending stiffness ($K_b$) is the resistance of a bone to bending and can be measured, for example, by QMT by applying submaximal loads and measuring the slope of the force displacement curve in the elastic region of the bone.

QMT is thus limited in that it can only be used on excised bones and bone samples. More particularly, although QMT can make direct measurements of bone bending strength and stiffness, its use in vivo is limited in that: (1) QMT is not able to differentiate between skin and bone compression, which may result in an inaccurate estimation of displacement; and (2) measurement of bone strength by QMT requires fracturing of the bone. Thus, the inventors recognize a need for improved methods and systems for assessing the stiffness of bone in vivo.

SUMMARY

It is against this background that the present disclosure provides methods for determining the stiffness of a bone and systems for estimating the stiffness of a bone in vivo.

In various embodiments, a parametric model based computer implemented method for determining the stiffness of a bone is disclosed. The computer implemented method includes (1) applying a superposition of static and oscillatory forces (F) over a range of frequencies (f) to a region of a skin-bone complex thereby exciting oscillatory accelerations (a) over the range of frequencies (f) of the skin-bone complex; (2) receiving measurements of the oscillatory forces (F) as functions of time F(t) and the resulting oscillatory accelerations (a) as functions of time a(t) with a data receiver communicatively coupled to a controller including a processor and a storage medium containing computer readable and executable instructions; (3) repeating step (1)-(2), wherein the static and oscillatory forces (F) in step (1) are applied to a shifted region of the skin-bone complex; (4) repeating step (3) until an optimized data set is determined; and (5) determining the stiffness of the bone from ($k_b$) values of the optimized data set. When executed by the processor, the computer readable and executable instructions cause the controller to automatically: (i) transform a(t) and F(t) to functions of frequency, a(f) and F(f), (ii) reduce a(f) and F(f) to accelerance frequency response function data A(f), (iii) determine, a complex compliance frequency response function, Y(f) and associated complex stiffness frequency response function H(f), (iv) fit a parametric mathematical model to Y(f) to obtain a first set of parameters of the parametric mathematical model, including the stiffness of the bone ($K_B$), (v) fit the parametric mathematical model to H(f) to obtain a second set of parameters of the parametric mathematical model, including the stiffness of the bone ($K_B$), (vi) determine discrepancies between the first set of parameters and the second set of parameters as a measure of conformity thereof to the parametric mathematical model, and (vii) save the measure of conformity, the first set of parameters, and the second set of parameters as a data set.

In other embodiments, a system for estimating the stiffness of a bone in vivo is disclosed. The system includes a device for measuring the stiffness of the bone in vivo and a data analyzer. The device for measuring the stiffness of the bone in vivo includes a bone positioning support, a mechanical force applicator, and a frequency response recorder, in which the bone positioning support is configured to position and support a skin-bone complex in an orientation and position for measurement. The mechanical force applicator includes a force transducer and a force probe and is configured to apply a superposition of static and oscillatory forces (F) over a range of frequencies (f) to a region of the skin-bone complex, wherein the oscillatory forces (F) excite oscillatory accelerations (a) of the skin-bone complex. The frequency response recorder is configured to measure and transmit to the data analyzer the oscillatory forces as functions of time F(t) and the oscillatory accelerations as functions of time a(t). The data analyzer is communicatively coupled to the force transducer and frequency response recorder. The data analyzer includes a storage medium containing computer readable and executable instructions for collecting the transmitted oscillatory forces as functions of time F(t) and oscillatory accelerations as functions of time a(t) of the skin-bone complex, the storage medium storing a parametric mathematical model of the skin-bone complex. The data analyzer also includes a processor for executing the instructions to transform a(t) and F(t) to functions of frequency, a(f) and F(f), to reduce a(f) and F(f) to accelerance frequency response data A(f), to determine a complex compliance frequency response function Y(f) and associated complex stiffness frequency response function H(f), to fit the parametric mathematical model to Y(f) to obtain a first set of parameters of the parametric mathematical model, including the stiffness of the bone ($K_B$), to fit the parametric mathematical model to H(f) to obtain a second set of parameters of the parametric mathematical model, including the stiffness of the bone ($K_B$), and to determine the discrepancies between the first set of parameters and the second set of parameters as a measure of conformity thereof to the parametric mathematical model.

In yet other embodiments, a method for determining the stiffness of a bone is disclosed. The method includes (1) applying a controlled superposition of static and oscillatory forces (F) measured as a first function of frequency F(f) over a range of frequencies to a skin-bone complex in vivo, thereby exciting oscillatory accelerations (a) over the range of frequencies of the skin-bone complex; (2) measuring the resulting oscillatory accelerations (a) of the skin-bone complex as a second function of frequency a(f); (3) transforming F(f) and a(f) to obtain the stiffness of the skin-bone complex as a function of frequency H(f); (4) transforming F(f) and a(f) to obtain the compliance of the skin-bone complex as a function of frequency Y(f); (5) fitting a parametric model to H(f) to obtain a first set of parameters of the parametric model, including the stiffness of the bone ($K_B$); (6) fitting the parametric model to Y(f) to obtain a second set of parameters of the parametric model, including the stiffness of the bone ($K_B$); (7) determining discrepancies between the first set of parameters and the second set of parameters as a measure of conformity thereof to the parametric mathematical model; (8) saving the measure of conformity, the first set of parameters, and the second set of parameters as a data set; (9) repeating steps (1)-(8), wherein the static and oscillatory forces (F) in step (1) are applied to a shifted region of the skin-bone complex; (10) repeating step (9) until an optimized data set is determined; and (11) determining the stiffness of the bone from ($K_B$) values of the optimized data set.

BRIEF DESCRIPTION OF THE DRAWINGS

A more complete appreciation of the invention and the many embodiments thereof will be readily obtained as the same becomes better understood by reference to the following detailed description when considered in connection with the accompanying drawings, wherein.

Figure 1:
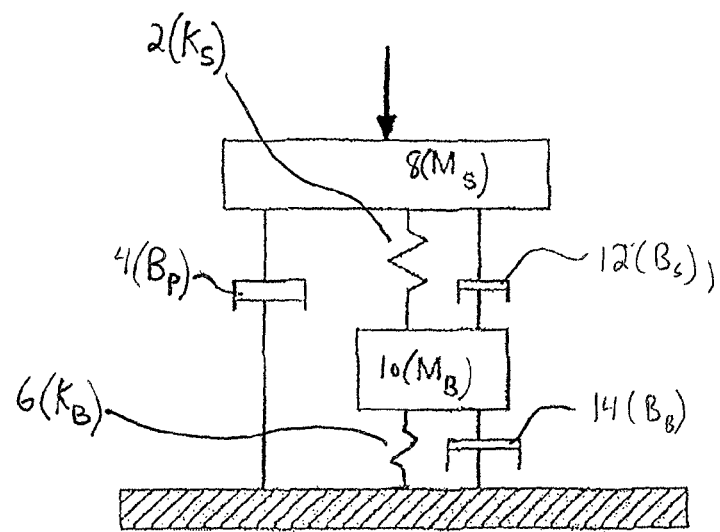
FIG. 1 depicts a schematic of a model of a skin-bone complex.

The provided drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several embodiments of the invention, and together with the description serve to explain the principles of the invention; it being understood, however, that the invention is not limited to the precise arrangements shown.

DETAILED DESCRIPTION OF THE INVENTION

Specific embodiments of the present application will now be described. The invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art. The terminology used in the description herein is for describing particular embodiments only and is not intended to be limiting. As used in the specification and appended claims, the singular forms "a," "an," and "the" are intended to include the plural forms as well, unless the context clearly indicates otherwise.

Recitations of "at least one" component, element, etc. in the present disclosure and appended claims should not be used to create an inference that the alternative use of the articles "a" or "an" should be limited to a single component, element, etc.

In the present disclosure and appended claims, recitations of a component being "configured" to embody a particular property, or function in a particular manner, are structural recitations, as opposed to recitations of intended use. More specifically, references to the manner in which a component is "configured" denotes an existing physical condition of the component and, as such, is to be taken as a definite recitation of the structural characteristics of the component.

As used in the present disclosure and appended claims, terms like "preferably," "commonly," and "typically" are not utilized to limit the scope of the claims or to imply that certain features are critical, essential, or even important to the structure or function of the claimed embodiments. Rather, these terms are merely intended to identify particular aspects of an embodiment of the present disclosure or to emphasize alternative or additional features that may or may not be utilized in a particular embodiment of the present disclosure.

The terms "substantially" and "approximately," as used in the present disclosure and appended claims, represent the inherent degree of uncertainty that may be attributed to any quantitative comparison, value, measurement, or other representation. Such terms are also utilized to represent the degree by which a quantitative representation may vary from a stated reference without resulting in a change in the basic function of the subject matter at issue.

Unless otherwise indicated, all numbers expressing quantities, properties, conditions, and so forth as used in the specification and claims are to be understood as being modified in all instances by the term "about." Additionally, the disclosure of any ranges in the specification and claims are to be understood as including the range itself and also anything subsumed therein, as well as endpoints. Notwithstanding that numerical ranges and parameters setting forth the broad scope of the disclosure are approximations, the numerical values set forth in the specific examples are reported as precisely as possible. Any numerical values, however, inherently contain certain errors necessarily resulting from error found in their respective measurements.

"Automatically" includes the use of a machine to conduct a particular action. The process by which data is extracted, organized and stored is a data-driven and largely automatic process and may utilize a computer network (e.g., wide area network, such as the internet, a local area network, a mobile communications network, a public service telephone network, and/or any other network) and may be configured to electronically connect a user computing device (e.g., a PC) and a server computing device (e.g., cloud, mainframe, or other server device).

"Calculate" includes automatically determining or ascertaining a result.

"Computer" includes a machine (e.g., desktop, laptop, tablet, smartphone, television, server, as well as other current or future computer instantiations) containing a computer processor that has been specially configured with a set of computer executable instructions. References to "at least one" computer are intended to encompass both autonomous systems and sub-systems as well as situations where a given functionality might be divided across multiple machines (e.g. parallel processing) for efficiency or other purposes.

"Data Receiver" as used herein includes any component configured to receive data.

"Exemplary" as used herein means giving an example; serving as an illustration or example of something.

"GUI" or "Graphical User Interface" includes a user interface displayed on a visual subsystem (e.g., desktop monitor, tablet/phone screen, interactive television screen, etc.) by which users interact with electronic devices via images (e.g., lists, hyperlinks, panels, etc.).

"Parametric Mathematical Model" as used herein includes any mathematical model which can be described using a finite number of parameters.

A "Processor" may include any processing component configured to receive and execute instructions (such as from the data storage component and/or memory component). Network interface hardware may include any wired/wireless hardware generally known to those of skill in the art for communicating with other networks and/or devices.

"Root Mean Square," also known as the quadratic mean and abbreviated RMS, as used herein is a statistical measure of the magnitude of a varying quantity and is calculated as the square root of the arithmetic mean (average) of the squares of the original values.

A "Skin-Bone Complex" as used herein is bone and the overlying soft tissue including skin and muscle.

A "Server" may be specially configured or configured as a general purpose computer with the requisite hardware, software, and/or firmware. A server may include a processor, input/output hardware, network interface hardware, a data storage component (which stores data and/or metadata) and a memory component configured as volatile or non-volatile memory including RAM (e.g., SRAM, DRAM, and/or other types of random access memory), flash memory, registers, compact discs (CDs), digital versatile discs (DVD), and/or other types of storage components. A memory component may also include operating logic that, when executed, facilitates the operations described herein. An administrative computing device may also be employed to facilitate manual corrections to the metadata.

"Viscoelastic Material" as used herein includes material that has both damping and compressible properties.

In embodiments, a parametric model based computer implemented method for determining the stiffness of a bone is disclosed. Stiffness, as used herein, is the mechanical property measuring the resistance offered by an elastic body to deformation. It can be represented by $F/\delta$, wherein F is the force applied to the body and $\delta$ is the displacement produced by the force. In some embodiments, the computer implemented method utilizes Mechanical Response Tissue Analysis (MRTA). In one or more embodiments, Mechanical Response Tissue Analysis involves a two-step technique for measuring the mechanical properties (i.e., mass, stiffness and damping) of long bones, such as, e.g., the ulna or the humerus in the human arm or the tibia or femur in the human leg. While the present disclosure is applicable to numerous bones in the body, for purposes of conveniently describing certain embodiments thereof, reference will be made to the ulna. However, one of skill in the art will recognize that reference to the ulna is not intended to be limiting. The first step of MRTA generally involves the collection of data in the form of a complex accelerance frequency response function, A(f). The second step of MRTA generally involves the analysis of this complex accelerance frequency response function, A(f) by fitting A(f) to a parametric mathematical model of the skin-bone complex to estimate the values of mechanical properties thereof. The parametric mathematical model takes the form of a complex rational polynomial. The purpose of the disclosed embodiments is to facilitate the collection of a complex accelerance frequency response function, A(f) that conforms well to the parametric mathematical model.

Figure 2:
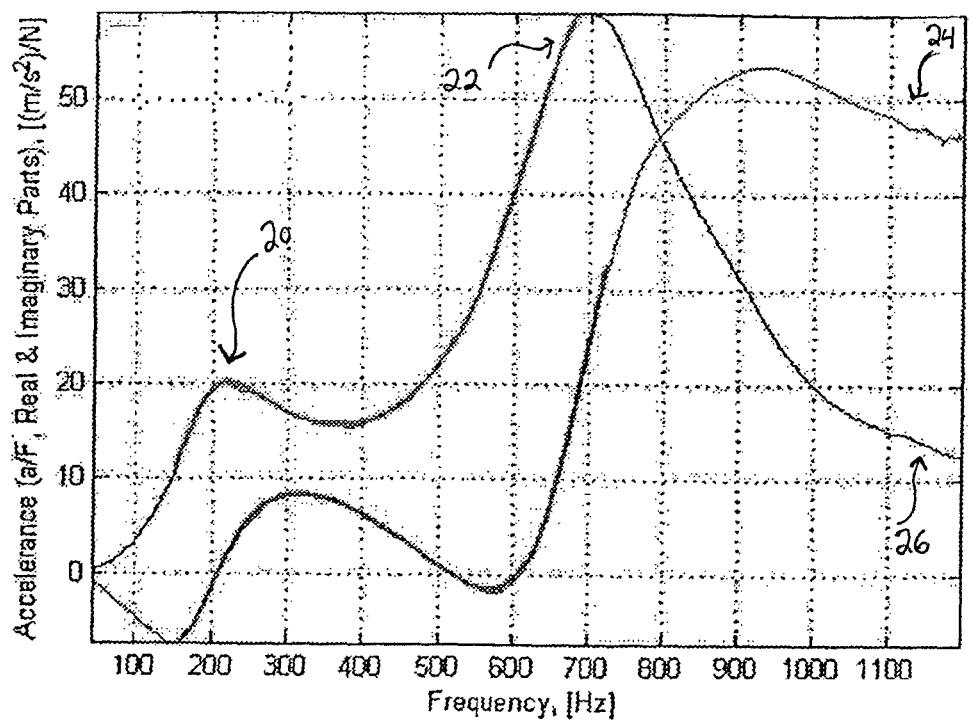
FIG. 2 depicts acceleration frequency response function data A(f) and the parametric mathematical model best fit.

With reference to FIG. 2, in some embodiments, the first step of MRTA involves collecting data in the form of a complex accelerance frequency response function, A(f) of a skin-bone complex. The skin-bone complex is bone and the overlying soft tissue including skin and muscle. In some embodiments, the complex accelerance frequency response function, A(f), data are collected by: (1) positioning a force probe on the skin overlying the bone, (2) applying both (i) a static force and (ii) oscillatory forces (F), (3) varying the frequency of the oscillatory forces (F) over a sub-range of the auditory frequency range, (4) measuring (i) the force applied through the force probe to the skin and (ii) the resulting acceleration of the force probe on the skin to obtain an oscillatory acceleration (a) of the skin-bone complex, and (5) calculating accelerance (i.e., acceleration divided by force) as a complex function of frequency, i.e., the complex accelerance frequency response function, A(f).

A "complex" function of frequency is one that records both (1) the magnitude of the oscillatory acceleration (a) that occurs in response to the applied oscillatory forces (F) relative to the magnitude of the oscillatory forces (F), and (2) the phase delay between the peak of the oscillatory forces (F) and the peak of the oscillatory acceleration (a). Mathematically equivalently, the magnitude and phase delay of a "complex" function of frequency may be expressed and recorded as a real part 26 and an imaginary part 24, wherein the real part 26 is equal to the magnitude multiplied by the cosine of the phase delay, and the imaginary part 24 is equal to the magnitude multiplied by the sine of the phase delay.

In some embodiments, the second step in MRTA involves analysis of the complex accelerance frequency response function, A(f), to determine the mechanical properties of the bone. Such analysis includes fitting the complex accelerance frequency response function, A(f) to the parametric mathematical model. The parametric mathematical model represents the behavior of the skin-bone complex. Referring to FIG. 1, in one or more embodiments, the parametric mathematical model includes 7 parameters and accounts for the mass, stiffness, and damping of the skin and bone as well as parallel damping of soft tissues. Specifically, the 7-parameter model accounts for mass of the skin 8 ($M_S$), transverse bending stiffness of the skin 2 ($K_S$), damping coefficient of the skin 12 ($B_S$), mass of the bone 10 ($M_B$), transverse bending stiffness of the bone 6 ($K_B$), damping coefficient of the bone 14 ($B_B$), and damping coefficient of the surrounding soft tissue 4 ($B_P$). These parameters may alternatively be referenced using lowercase letters, e.g. ($m_s$), ($k_s$), ($b_s$), ($m_b$), ($k_b$), ($b_b$), and ($b_p$). While the present disclosure is applicable to numerous parametric mathematical models, for purposes of conveniently describing certain embodiments thereof, reference will be made to the 7-parameter model. However, one of skill in the art will recognize that reference to the 7-parameter model is not intended to be limiting and that the methods and systems disclosed herein may be applicable to alternate parametric mathematical models.

In some embodiments, the parametric mathematical model of the skin-bone complex is in the form of a ratio of complex polynomials in which the variable is frequency and the lowest power of frequency in the polynomial in the numerator is zero. In the mathematical expression of A(f), the lowest power of frequency in the polynomial is two. Therefore, before the parametric model can be fitted, A(f) is first converted to a form in which the lowest power of frequency in the numerator polynomial is zero. Such a form is obtained by integrating A(f) twice with respect to frequency yielding a complex compliance frequency response function, $Y(f)=x(f)/F(f)$ in which "x" is displacement. Such a form can also be obtained by inverting Y(f) to obtain the associated complex stiffness frequency response function, $H(f)=F(f)/x(f)$.

The differential equations of motion representing the parametric mathematical model with 7-parameters are:

$$F - K_S(x_S - x_B) - B_S\left(\frac{dx_S}{dt} - \frac{dx_B}{dt}\right) - B_P\frac{dx_S}{dt} = M_S\frac{d^2x_S}{dt^2}$$

$$K_S(x_S - x_B) - K_Bx_B + B_S\left(\frac{dx_S}{dt} - \frac{dx_B}{dt}\right) - B_B\frac{dx_B}{dt} = M_B\frac{d^2x_B}{dt^2}$$

As $H(f) = \text{Real}\{H(f)\} + j\,\text{Imag}\{H(f)\}$, wherein $\omega = 2\pi f$, $H(f)$ can be determined in terms of things which are known and measurable. Specifically, $$\text{Real}\{H(\omega)\} = \frac{M_S[(C_0 - \omega^2)(\omega^4 - A_2\omega^2 + A_0) - C_1\omega(A_3\omega^3 - A_1\omega)]}{(C_0 - \omega^2)^2 + (C_1\omega)^2}$$

$$\text{Imag}\{H(\omega)\} = \frac{M_S[C_1\omega(\omega^4 - A_2\omega^2 + A_0) + (C_0 - \omega^2)(A_3\omega^3 - A_1\omega)]}{(C_0 - \omega^2)^2 + (C_1\omega)^2}$$

wherein, $$A_0 = \frac{K_S K_B}{M_S M_B}$$

$$A_1 = \frac{[K_B(B_S + B_P) + K_S(B_B + B_P)]}{M_S M_B}$$

$$A_2 = \frac{(K_S + K_B)}{M_B} + \frac{K_S}{M_S} + \frac{[B_S(B_B + B_P) + B_B B_P]}{M_S M_B}$$

$$A_3 = \frac{(B_S + B_P)}{M_B} + \frac{(B_S + B_P)}{M_S}$$

$$C_1 = \frac{(B_S + B_B)}{M_B}$$

$$C_0 = \frac{(K_S + K_B)}{M_B}$$

Inverting the associated complex stiffness frequency response function, H(f), generates complex compliance frequency response function, Y(f).

Utilizing basic algebraic manipulation, the values for each of the 7 parameters can be determined from the fitted regression coefficients, $A_0$, $A_1$, $A_2$, $A_3$, $C_1$, and $C_0$. In embodiments, the determination of each of the 7 parameters is independently made from Y(f) and from H(f).

In theory, for data conforming perfectly to the 7-parameter model, fitting the 7-parameter model to Y(f) and H(f) should yield exactly the same values for each of the 7 parameters. However, in practice the values of the 7 parameters vary between those obtained from Y(f) and those obtained from H(f). Therefore, the extent to which these values of the 7 parameters differ from one another is a measure of the extent to which the data do not conform to the 7-parameter model.

In embodiments, the static force applied to the skin overlying the bone serves at least two functions. As approximated by the 7-parameter model of the skin-bone complex of the forearm, the skin-bone complex has two resonances, the properties of which are determined primarily, but not entirely, by the bone in one case and by the skin and other soft tissue between the surface of the skin and the bone in the other case. The first function of the static load is to exceed the amplitude of the oscillatory forces (F), so that the force probe does not separate from the arm on every negative phase of the oscillatory forces (F). The second function of the static load is to compress the soft tissue overlying the ulna, squeezing tissue fluid out from between the surface of the skin and the underlying bone, thereby increasing the stiffness and reducing the mass of this tissue. Because the resonant frequency of a mechanical system is proportional to the square root of the system's effective stiffness divided by its effective mass, increasing the static load increases the frequency of the resonance associated with the skin, separating it from the resonance associated with the ulna, and thereby improving the ability to more accurately estimate the mechanical properties of the bone and skin. The magnitude of the static load that optimizes these estimates varies with individual differences in the amount of soft tissue between the surface of the skin and the underlying ulna, and is best determined by iteratively collecting and analyzing data, and adjusting the static load in such a manner as to maximize conformity of the data to the 7-parameter model. In various embodiments, the static load varies between approximately 3 N and approximately 30 N. Static loads lower than approximately 3 N are generally insufficient, even in lean patients and static loads greater than approximately 30 N are painful, even in obese or muscular people. In other embodiments the range of static loads varies within a subrange of approximately 3 N and approximately 30 N, such as between approximately 3 N and approximately 25 N, between approximately 5 N and approximately 30 N or, between approximately 10 N and approximately 20 N.

In embodiments of a parametric model based computer implemented method for determining the stiffness of a bone the method initially comprises applying a superposition of static and oscillatory forces (F) over a range of frequencies (f), i.e. vibrations, to a region of the skin-bone complex of a bone of interest, e.g., the ulna. The oscillatory forces (F) applied to the skin-bone complex induce corresponding oscillatory accelerations (a) over the range of frequencies (f) of the skin-bone complex. Further, a data receiver receives measurement of the oscillatory forces as functions of time F(t) and the resulting oscillatory accelerations (a) as functions of time a(t). The data receiver is communicatively coupled to a controller. Communicatively coupled means electrically, signally, wirelessly, wired, optically, or similarly connected. The controller comprises a processor and a storage medium containing computer readable and executable instructions which, when executed by the processor, cause the controller to automatically execute a series of analysis steps to determine the stiffness of the bone based on the measured oscillatory forces as functions of time F(t) and the resulting oscillatory accelerations as functions of time a(t).

Figure 3:
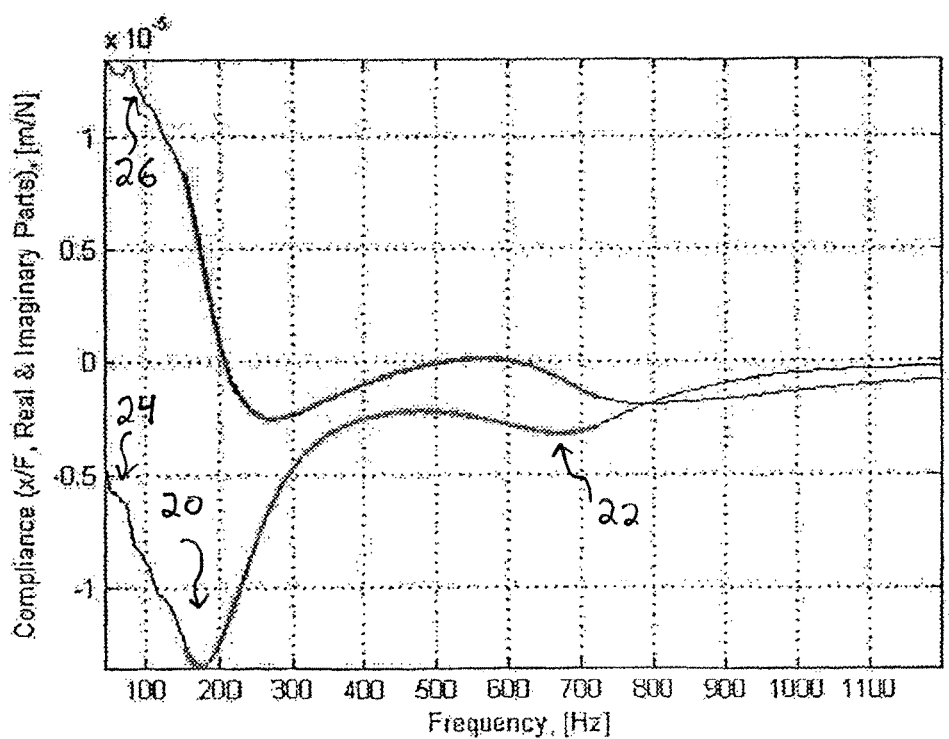
FIG. 3 depicts complex compliance frequency response function Y(f) and the parametric mathematical model best fit.
Figure 4:
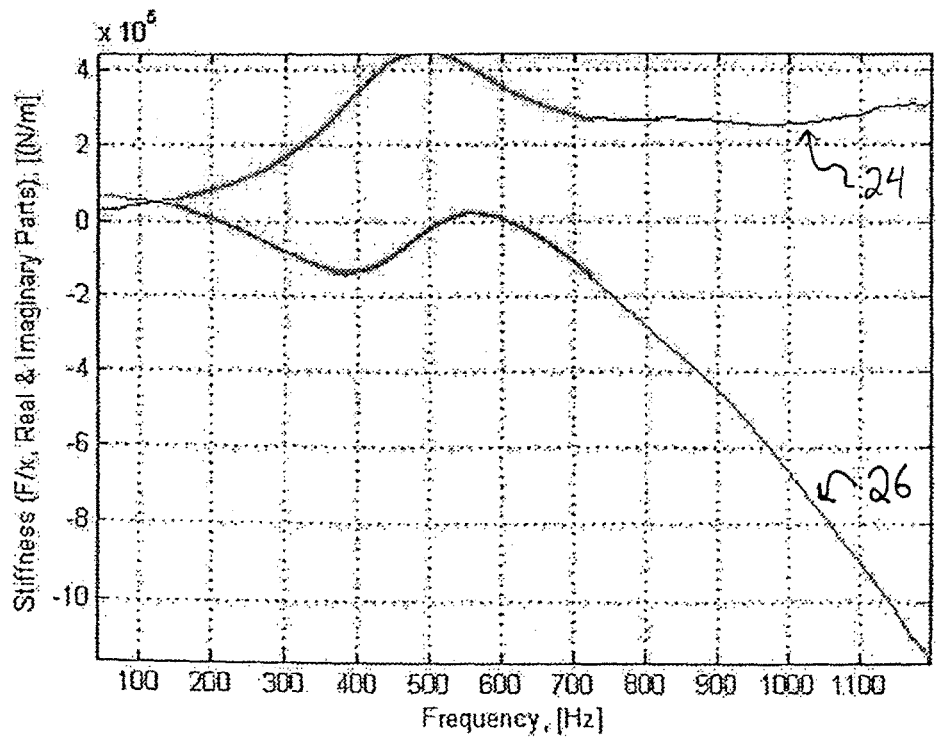
FIG. 4 depicts complex stiffness frequency response function H(f) and the parametric mathematical model best fit.

With reference to FIGS. 3 and 4, the controller, in accordance with the executable instructions on the storage medium containing computer readable and executable instructions, automatically determines the oscillatory acceleration (a) and oscillatory forces (F) as functions of frequency, a(f) and F(f) respectively by performing Fourier transformations to convert a(t) and F(t) to a(f) and F(f) respectively. Additionally, the controller automatically determines the complex compliance frequency response function, Y(f) and the associated complex stiffness frequency response function H(f). In embodiments Y(f) and H(f) are determined by reducing a(f) and F(f) to the complex accelerance frequency response function A(f) and integrating A(f) twice in accordance with the mathematical manipulation previously discussed. Additionally, the controller automatically fits a parametric mathematical model to Y(f) to obtain a first set of parameters of the parametric mathematical model, including the stiffness of the bone ($K_B$), as well as fits the parametric mathematical model to H(f) to obtain a second set of parameters of the parametric mathematical model, including the stiffness of the bone ($K_B$). The parametric mathematical model may also be as previously discussed. The controller further automatically determines discrepancies between the first set of parameters and the second set of parameters as a measure of conformity thereof to the parametric mathematical model and saves the measure of conformity, the first set of parameters, and the second set of parameters as a data set.

As shown in FIGS. 2, 3, and 4, when the measure of conformity indicates a good fit, the fit parametric mathematical model conforms to the collected data closely. Specifically, between approximately 150 Hz and 725 Hz, the fit parametric mathematical model can be seen graphically overlaid over the empirical A(f), Y(f), and H(f) in FIG. 2, FIG. 3, and FIG. 4 respectively. Additionally, both the imaginary part 24 and the real part 26 of each of A(f), Y(f), and H(f) are shown.

In various embodiments the saving of the measure of conformity, the first set of parameters, and the second set of parameters as a data set is completed using the storage medium. In some embodiments every data set generated is saved and retained in the storage medium. In further embodiments, only a predetermined number of data sets are retained in the storage medium and as new data sets are generated the oldest data sets are deleted and/or written over. In still further embodiments, in lieu of, or in addition to, saving the data sets to the storage medium the data sets are physically printed such that hard copies of the measure of conformity, the first set of parameters, and the second set of parameters in each data set are generated. In yet further embodiments, the data sets are saved on a storage medium located in a server external to the system.

In other embodiments the data set also includes a record of Y(f), H(f), or Y(f) and H(f). Retaining the raw data representing Y(f) and/or H(f) allows repeated or alternative analysis to be performed at a later time.

Further, in an effort to obtain an optimized data set, the static and oscillatory forces (F) are applied to a shifted region of the skin-bone complex and the data receiver receives measurement of the oscillatory forces as functions of time F(t) and the resulting oscillatory accelerations (a) as functions of time a(t). for the shifted region. The controller, in accordance with the executable instructions on the storage medium containing computer readable and executable instructions, automatically determines the oscillatory acceleration (a) and oscillatory forces (F) as functions of frequency, a(f) and F(f) respectively by performing Fourier transformations to convert a(t) and F(t) to a(f) and F(f) respectively for the shifted region. Additionally, the controller automatically determines the complex compliance frequency response function, Y(f) and the associated complex stiffness frequency response function H(f) for the shifted region. In embodiments Y(f) and H(f) are determined by reducing a(f) and F(f) to the complex accelerance frequency response function A(f) and integrating A(f) twice in accordance with the mathematical manipulation previously discussed. Additionally, the controller automatically fits the parametric mathematical model once again to the Y(f) to obtain a new iteration of the first set of parameters of the parametric mathematical model, including the stiffness of the bone ($K_B$), as well as fits the parametric mathematical model to H(f) to obtain a new iteration of the second set of parameters of the parametric mathematical model, including the stiffness of the bone ($K_B$). The controller further automatically determines discrepancies between the new iterations of the first set of parameters and the second set of parameters as a measure of conformity thereof to the parametric mathematical model and saves the measure of conformity, the first set of parameters, and the second set of parameters as a data set. Repetition of collection of the oscillatory forces (F) and the resulting oscillatory accelerations (a) for shifted regions and analysis of the collected oscillatory forces (F) and oscillatory accelerations (a) to determine parameters of the parametric mathematical model is continued until the optimized data set is determined.

In various embodiments the static force applied to the skin-bone complex is adjusted for some or all repetitions of collection of the oscillatory forces (F) and the resulting oscillatory accelerations (a) for the shifted regions.

In various embodiments one or more layers of a viscoelastic material is applied over the skin-bone complex. In other embodiments one or more layers of a viscoelastic material is applied under the skin-bone complex between the skin-bone complex and the structure upon which the skin-bone complex rests. In still other embodiments one or more layers of a viscoelastic material is applied both over the skin-bone complex and between the skin-bone complex and the structure upon which the skin-bone complex rests.

In an embodiment, the optimized data set is determined based on the measure of conformity. If, when the superposition of static and oscillatory forces (F) over a range of frequencies (f) are applied to a shifted region of the skin-bone complex the measure of conformity of the first set of parameters and the second set of parameters is improved, the first set of parameters and the second set of parameters of the shifted region are believed to represent an improved representation of the true parameters of the bone over the previous sets of parameters. The repetition of collection of the oscillatory forces (F) and the resulting oscillatory accelerations (a) for shifted regions and analysis of the collected oscillatory forces (F) and oscillatory accelerations (a) to determine parameters of the parametric mathematical model is continued until the measure of conformity is worsened. The worsening of the measure of conformity indicates the shifted region has traversed past the ideal region of the bone for data collection and the optimized data set is the immediately previously collected first set of parameters and second set of parameters. For example, the superposition of static and oscillatory forces (F) over a range of frequencies (f) may be initially applied to a region of the skin-bone complex medial of the centerline of the ulna, then the static and oscillatory forces (F) over a range of frequencies (f) are applied to a shifted region lateral of the initial region of the skin-bone complex, then the static and oscillatory forces (F) over a range of frequencies (f) are applied to a further shifted region further lateral of the initial region of the skin-bone complex. The measure of conformity improves upon each further lateral shift of the application of the static and oscillatory forces (F) until the optimum location for data collection is passed by. When the optimum location for data collection is passed by, the measure of conformity will worsen. The optimized data set with respect to medial to lateral shifting of the region is represented by the best measure of conformity of the saved data sets.

In other embodiments, a superposition of static and oscillatory forces (F) over a range of frequencies (f) are initially applied to a region of the skin-bone complex with the forearm at a particular angle of rotation with respect to its long axis, then static and oscillatory forces (F) over a range of frequencies (f) are applied to a region accessed by rotating the forearm on its long axis. The measure of conformity improves upon each further rotational shift of the application of the static and oscillatory forces (F) until the optimum location for data collection is passed by. When the optimum location for data collection is passed by, the measure of conformity will worsen. The optimized data set with respect to rotational shifting of the region is represented by the best measure of conformity of the saved data sets. Analogously, the region may be shifted longitudinally along the long axis of the forearm and an optimized data set with respect to longitudinal shifting of the region may be obtained. Furthermore, the magnitude of the static load, and thereby the position of the resonance determined primarily by the mechanical properties of the skin and soft tissues, may be varied and an optimized data set with respect to static load obtained. In addition, layers of viscoelastic material may be inserted between the skin and the force probe that applies force to the skin, and an optimized data set with respect to the number of layers obtained. In this way an overall optimized data set is identified.

Upon determination of the overall optimized data set, the stiffness of the bone can be determined. Additionally, in various embodiments, each of the individual optimized data sets may be used to determine the stiffness of the bone. Transverse bending stiffness of the bone ($K_B$) can be determined directly from the parametric parameters associated with the optimized data set. In embodiments, the determined stiffness of the bone is the transverse bending stiffness of the bone ($K_B$) generated from $Y(f)$ as part of the first set of parameters associated with the optimized data set. In other embodiments, the determined stiffness of the bone is the transverse bending stiffness of the bone ($K_B$) generated from $H(f)$ as part of the second set of parameters associated with the optimized data set. In still other embodiments, the determined stiffness of the bone is an average of the transverse bending stiffness of the bone ($K_B$) generated from $Y(f)$ as part of the first set of parameters associated with the optimized data set and the transverse bending stiffness of the bone ($K_B$) generated from $H(f)$ as part of the second set of parameters associated with the optimized data set. In yet still other embodiments, the determined stiffness of the bone is a weighted average of the transverse bending stiffness of the bone ($K_B$) generated from $Y(f)$ as part of the first set of parameters associated with the optimized data set and the transverse bending stiffness of the bone ($K_B$) generated from $H(f)$ as part of the second set of parameters associated with the optimized data set.

Additionally, in multiple embodiments, the determined stiffness of bone in the method is flexural rigidity, EI, and may be calculated based on the determined transverse bending stiffness 6 ($K_B$) of the bone. Specifically, $EI=K_B L^3/48$, wherein L is the length of the bone.

In various embodiments, the measure of conformity between the first set of parameters and the second set of parameters is quantified as a root mean square (RMS) therebetween of the percentage differences between the seven parameters estimated from $Y(f)$ and $H(f)$, i.e. percentage root mean square (% RMS).

Additionally, in accordance with the 7-parameter model, each of the parameters must have a positive value in the optimized data set. Specifically, mass of the skin 8 ($M_S$), transverse bending stiffness of the skin 2 ($K_S$), damping coefficient of the skin 12 ($B_S$), mass of the bone 10 ($M_B$), transverse bending stiffness of the bone 6 ($K_B$), damping coefficient of the bone 14 ($B_B$), and damping coefficient of the surrounding soft tissue 4 ($B_P$) are all by definition positive values. Thus, in embodiments, if the first set of parameters or the second set of parameters include a negative parameter value it is known that the sets of parameters are not ideal and thus do not represent the optimized data set.

Further, with reference to FIG. 3, the area under the imaginary part of the compliance curve between 40 Hz and 100 Hz is preferably less than $6\times10^{-4}$ m/Ns. In the 7-parameter model, the imaginary part of compliance approaches zero as frequency approaches zero. If the sub-range of frequency that minimizes % RMS does not include frequencies below 100 Hz, then departure from this feature of the 7-parameter model will not be detected by % RMS alone. Therefore, for greater confidence in conformity to the 7-parameter model, the area under the imaginary part of the compliance curve between 40 Hz and 100 Hz should be substantially less than approximately $6\times10^{-4}$ m/Ns=$1\times10^{-5}$ m/N×60 Hz. If the imaginary part of compliance does not approach zero as frequency approaches zero the collected data is believed to be suboptimal.

In further embodiments, the oscillatory forces (F) are applied to the skin-bone complex through an excitation frequency range. In embodiments, the excitation frequency range has a minimum frequency of approximately 40 Hz and a maximum frequency of approximately 1200 Hz. In further embodiments, the excitation frequency range has a minimum frequency of approximately 80 Hz and a maximum frequency of approximately 1100 Hz. In still further embodiments, the excitation frequency range has a minimum frequency of approximately 100 Hz and a maximum frequency of approximately 1000 Hz.

In various embodiments, the excitation frequency range is selected such that the lower end or minimum frequency of the excitation frequency range is substantially less than the frequency of the bone peak 20 resonance frequency in the imaginary part 24 of the compliance frequency response function, and the upper end or maximum frequency of the excitation frequency range is substantially above the frequency of the skin peak 22 resonance frequency in the imaginary part 24 of the compliance frequency response function.

In various embodiments, the oscillatory forces (F) are applied over the excitation frequency range in a swept sine waveform, a pseudorandom waveform, a shaped random waveform, a chirp waveform, a burst waveform, a burst random waveform, a shaped burst random waveform, a white noise waveform, a pink noise waveform, or other standard waveforms known to one of ordinary skill in the art.

In various embodiments, the parametric mathematical model is fit to $Y(f)$ and $H(f)$ at a plurality of subranges within the excitation frequency range. In theory, for data conforming perfectly to the 7-parameter model, fitting the 7-parameter model to either $Y(f)$ or $H(f)$ should yield exactly the same estimates of the 7 parameters regardless of the frequency range over which the model is fitted; however, in practice it does not. Fitting the parametric mathematical model at a plurality of subranges produces a plurality of first and second sets of parameters and thus the subrange with the best measure of conformity for the first and second set of parameters may be selected. Specifically, in embodiments, the controller fits the 7-parameter model to both $Y(f)$ and $H(f)$ over a large number of frequency subranges with varying low starting frequencies, i.e., minimum frequencies, and varying high ending frequencies, i.e., maximum frequencies. Fitting the 7-parameter model to both $Y(f)$ and $H(f)$ produces a plurality of first and second sets of parameters. The controller then instructs the processor to calculate the percentage root mean square of the differences between the first and second sets of parameters for each frequency subrange and reports the minimum percentage root mean square as a measure of the extent to which $A(f)$ departs from the form of the 7-parameter model.

In further embodiments, the plurality of subranges within the excitation frequency range are generated by increasing the minimum frequency in repeated intervals and reducing the maximum frequency in repeated intervals. For example, in some embodiments, the minimum frequency is increased in approximately 5 Hz intervals and the maximum frequency is reduced in approximately 25 Hz intervals. With a excitation frequency range of approximately 40 Hz to approximately 1200 Hz a non-exhaustive listing of approximations of the subranges includes 45 Hz to 1200 Hz, 50 Hz to 1200 Hz, 55 Hz to 1200 Hz, 60 Hz to 1200 Hz, 65 Hz to 1200 Hz, 70 Hz to 1200 Hz, 40 Hz to 1175 Hz, 40 Hz to 1150 Hz, 40 Hz to 1125 Hz, 40 Hz to 1100 Hz, 40 Hz to 1075 Hz, 45 Hz to 1175 Hz, 45 Hz to 1150 Hz, 45 Hz to 1125 Hz, 45 Hz to 1100 Hz, 50 Hz to 1175 Hz, 50 Hz to 1150 Hz, 50 Hz to 1125 Hz, 50 Hz to 1100 Hz, and 50 Hz to 1075 Hz.

In further embodiments, various repeated intervals of increase for the minimum frequency ranging from approximately 1 Hz to approximately 20 Hz are envisioned and various repeated intervals of reduction for the maximum frequency ranging from approximately 5 Hz to approximately 50 Hz are envisioned with all permutations thereof specifically envisioned. For example, in some embodiments, the minimum frequency is increased in approximately 1 Hz intervals and the maximum frequency is reduced in approximately 5 Hz intervals, alternatively, the minimum frequency is increased in approximately 3 Hz intervals and the maximum frequency is reduced in approximately 10 Hz intervals, alternatively, the minimum frequency is increased in approximately 10 Hz intervals and the maximum frequency is reduced in approximately 20 Hz intervals, alternatively, the minimum frequency is increased in approximately 10 Hz intervals and the maximum frequency is reduced in approximately 30 Hz intervals, alternatively, the minimum frequency is increased in approximately 5 Hz intervals and the maximum frequency is reduced in approximately 20 Hz intervals, alternatively, the minimum frequency is increased in approximately 20 Hz intervals and the maximum frequency is reduced in approximately 50 Hz intervals.

In various embodiments, the minimum frequency is increased in repeated intervals until reaching a threshold minimum frequency. Similarly, the maximum frequency is reduced in repeated intervals until reaching a threshold maximum frequency. For example, in an embodiment, the minimum frequency is increased in approximately 5 Hz intervals until reaching a threshold minimum frequency of approximately 180 Hz and the maximum frequency is reduced in approximately 25 Hz intervals until reaching a threshold maximum frequency of approximately 700 Hz. In other embodiments, the threshold minimum frequency is 120, 140, 160, 180, or 200 and the threshold maximum frequency is 650, 700, 750, 800, or 850 with each combination thereof specifically envisioned. The threshold minimum and threshold maximum frequencies ensure that the plurality of subranges generated in the excitation frequency range all include the range between the threshold minimum frequency and the threshold maximum frequency as the minimum frequency is never higher than the threshold minimum frequency nor lower than the threshold maximum frequency. With reference to FIGS. 2 and 3, the threshold minimum and threshold maximum frequencies are selected such that the bone peak 20 of Y(f) and the skin peak 22 of Y(f) are contained within the frequency range enclosed by the threshold minimum frequency and the threshold maximum frequency. Typically, the bone peak 20 of Y(f) is centered at approximately 150-250 Hz and the skin peak of Y(f) is centered at approximately 500-800 Hz. In a further embodiment, the threshold minimum frequency is selected as the resonant frequency representing the bone peak and the threshold maximum frequency is selected as the resonant frequency representing the skin peak.

In various embodiments, each determination of the stiffness of the bone requires approximately 1 minute. Specifically, applying the superposition of static and oscillatory forces (F) over a range of frequencies (f) to a region of the skin-bone complex, receiving the oscillatory forces as functions of time F(t) and oscillatory accelerations as functions of time a(t), and the subsequent fitting of the parametric mathematical model to Y(f) and H(f) takes about 1 minute. The static and oscillatory forces (F) are then applied to the shifted region and a revised stiffness of bone is generated along with a revised measure of conformity; this measurement and analysis also requires approximately 1 minute. Typically, in some embodiments, approximately 15 measurements are made before the optimized data set is determined yielding an elapsed testing time of approximately 15 minutes for the patient.

Figure 5:
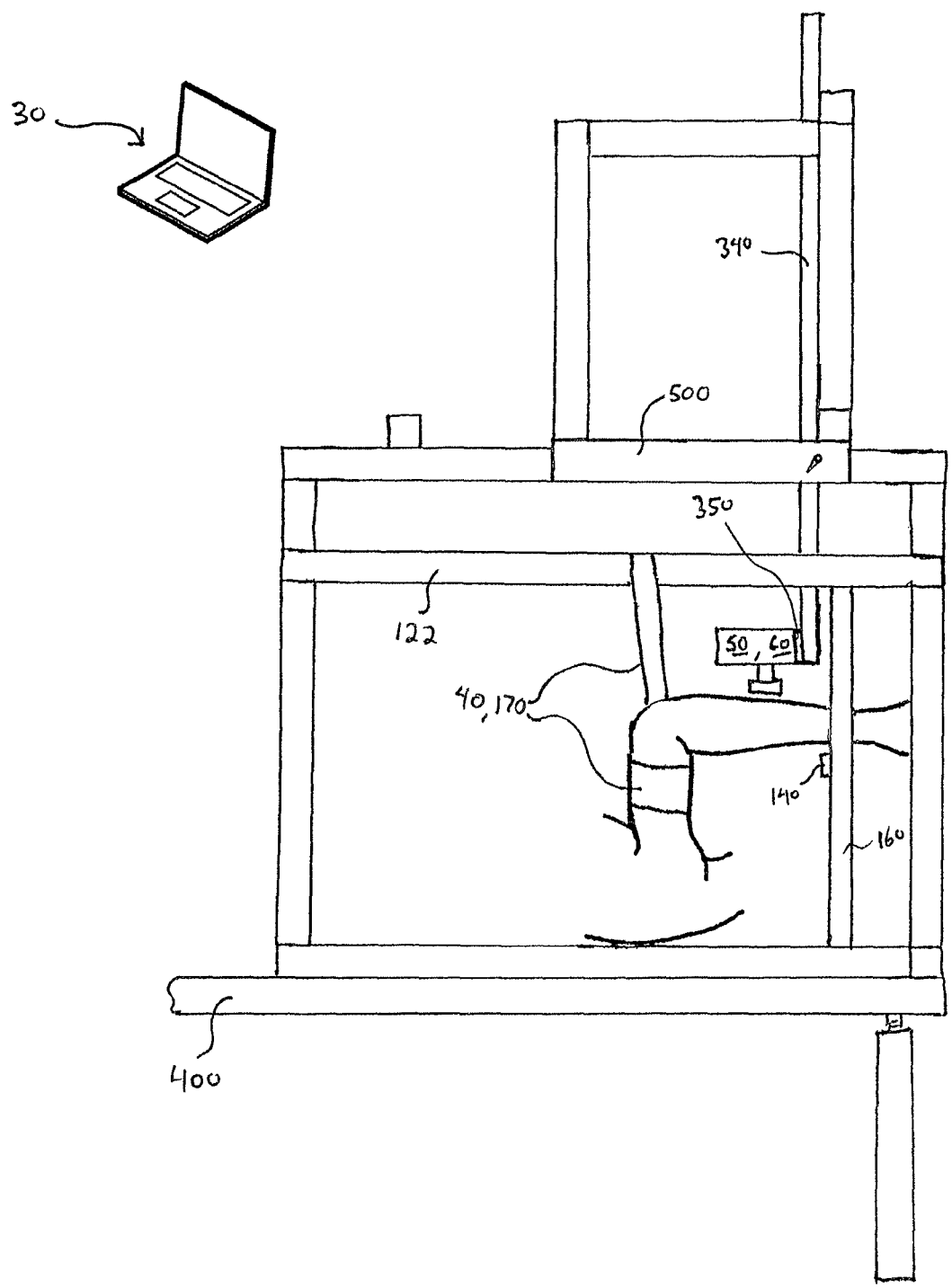
FIG. 5 depicts a side view of a system for estimating the stiffness of a bone in vivo according to at least one embodiment.
Figure 6:
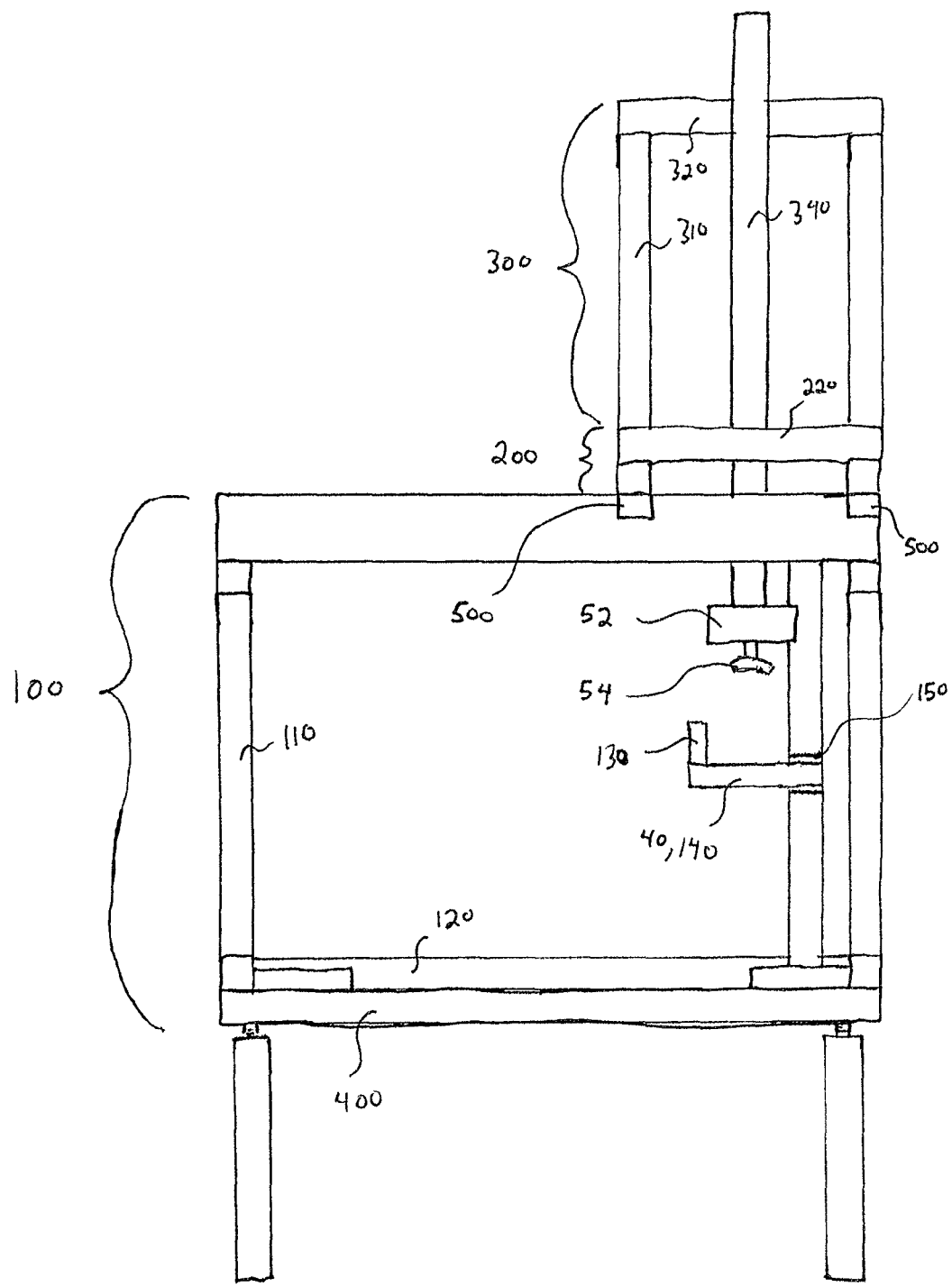
FIG. 6 depicts a front view of a system for estimating the stiffness of a bone in vivo according to at least one embodiment.

Referring to FIGS. 5 and 6, in further embodiments, a system for estimating the stiffness of a bone in vivo is provided. The system includes a device for measuring the stiffness of the bone in vivo as well as a data analyzer 30. In various embodiments the device for measuring the stiffness of the bone in vivo includes a bone positioning support 40, a mechanical force applicator 50, and a frequency response recorder 60. The bone positioning support 40 is configured to position and support the skin-bone complex in an orientation and position for measurement. The mechanical force applicator 50 includes a force transducer 52 and a force probe 54 and is configured to apply static and oscillatory forces (F) to a region of the skin-bone complex. The static and oscillatory forces (F) applied to the skin-bone complex by the mechanical force applicator 50 include oscillatory forces (F) which in turn create oscillatory accelerations (a) of the skin-bone complex. Finally, the frequency response recorder 60 is configured to measure and transmit to the data analyzer 30, e.g. a computer, the oscillatory forces (F) and the oscillatory accelerations (a).

In embodiments, the device for measuring the stiffness of the bone in vivo includes, in part, a first rigid, open framework 100 of rigidly interconnected vertical members 110 and horizontal members 120. In some embodiments, the open framework of rigidly interconnected vertical members 110 and horizontal members 120 that supports either of a patient's distal humeri, e.g., the distal humerus of the patient's right or left arm, below the elbow by means of the bone positioning support 40. In some embodiments the bone positioning support 40 includes a bone positioning harness 170. The bone positioning harness 170 is an adjustable and flexible but inelastic tensile sling. The bone positioning harness 170 is attachable to and/or attached to the open framework. In some embodiments, the bone positioning harness 170 is attachable to and/or attached to an elevated horizontal member 122 of the first rigid, open framework 100 such that it is suspended therefrom. In further embodiments, the bone positioning harness 170 is suspended from the open framework on the contralateral side of the patient's body so that the supported humerus is pulled medially against retarding muscular and ligamentous tension in the patient's own shoulder joint. In some embodiments the bone positioning support 40 includes a horizontal platform 140 to support the wrist. The wrist of the patient may be supported medially by a single vertical support peg 130 that extends from a horizontal platform 140 upon which the styloid process of the radius bone rests. In various embodiments, the horizontal platform 140 is selected from a set of such horizontal platforms 140 of varying preset heights. In further embodiments the horizontal platform 140 is attached to a platform carriage 150. The platform carriage 150 may be manually or electromechanically driven along, e.g., in an upward and/or downward direction, one or more platform vertical support members 160. In this way, the platform carriage 150 may function to adjust the vertical position, i.e., elevation, of the wrist and/or the horizontal position, i.e., orientation, of the ulna. The vertical members 110 may be secured to a rigid table 400 upon which the patient lies in a supine position. For example, the vertical member 110 may be secured to the rigid table 400 via suitable attachment devices, such as, e.g., via attachment bolts. The elevated horizontal members 122 from which the bone positioning harnesses 170 are suspended are rigidly attached to and supported by vertical members 110 of the open framework. The vertical members of the open framework may be secured to the rigid table 400 upon which the patient rests. For example, the vertical members of the open framework may be secured to the rigid table via suitable attachment devices, e.g., via attachment bolts.

In embodiments, the device for measuring the stiffness of the bone in vivo also includes, in part, a second open framework 200 of rigidly interconnected horizontal members 220. The second open framework 200 attaches to the first open framework 100 with a plurality of translatable clamps 500 such as slidable clamps or rollable clamps. The positioning of the second open framework 200 may be manually or electromechanically adjusted relative to the first open framework 100. In this way, the positioning of the second framework may be adjusted transversely across the patient's body.

In embodiments, the device for measuring the stiffness of the bone in vivo also further includes, in part, a third open framework 300 of rigidly interconnected vertical members 310 and horizontal members 320 supported by the second open framework 200. The third open framework 300 attaches to the second open framework 200 with a plurality of translatable clamps 500. The positioning of the third open framework 300 may be manually or electromechanically adjusted relative to the second open framework 200 perpendicularly relative to the direction of adjustment of the second open framework 200. In this way, the positioning of the third open framework 300 may be axially aligned with an axis extending along the length of the patient's body. In some embodiments, the third open framework 300 includes one or more carriage support vertical members 340 supporting a force applicator carriage 350 that may be manually or electromechanically driven therealong, e.g., in an upward and/or downward direction. In this way, the vertical positioning of the force applicator carriage 350 along the carriage support vertical members 340 and thereby the static preload force may be adjusted. Furthermore, in some embodiments, the force applicator carriage 350 supports the mechanical force applicator 50 and the frequency response recorder 60. More particularly, the force applicator carriage 350 supports orientation of the mechanical force applicator 50 and the frequency response recorder 60 so that the linear motion of the mechanical force applicator 50 is along a vertical direction.

The open, rigid 3-part framework, i.e., the first open framework 100, the second open framework 200, and the third open framework 300, permits the patient's shoulder, elbow, and wrist to be controllably positioned. The open, rigid 3-part framework also permits the position of the mechanical force applicator 50 and the frequency response recorder 60 to be controllably adjusted in three orthogonal dimensions, relative to the patient's forearm. With the open, rigid 3-part framework, a technician can quickly and precisely readjust the position of the mechanical force applicator 50 relative to the ulna for repeated data collection, such as, e.g., to a shifted position as previously discussed. To adjust the position of the mechanical force applicator 50 laterally across the patient's body, the second open framework 200 is loosened from the first open framework 100 and moved manually or electromechanically relative to the first open framework 100. To adjust the position of the mechanical force applicator 50 axially along the length of the patient's body, the third open framework 300 is loosened from the second open framework 200 and moved manually or electromechanically relative to the second open framework 200.

In further embodiments, the horizontal platform 140 configured to support a distal end of a human forearm comprises at least one layer of viscoelastic material thereon to dampen extraneous oscillatory forces (F) from the device. Dampening extraneous oscillatory forces (F) from the device may function to provide a cleaner and/or more pure data set that better conforms to the 7-parameter model.

In embodiments, the rigid table 400 has, or is rigidly attached to, mass in excess of 100 kg and a stiffness in excess of $1 \times 10^7$ N/m. Under ideal conditions, the rigid table 400 would have an infinite mass and stiffness. Further, in various embodiments, the open, rigid 3-part framework has a very large stiffness in excess of $1 \times 10^7$ N/m. The large mass and stiffness are desirable to minimize flexion and movement of the rigid table 400 and of the open, rigid 3-part framework during data collection. Movement of the rigid table 400 and/or the open, rigid 3-part framework is not accounted for in the parametric mathematical model and would introduce error into the collected data sets.

In various embodiments, the mechanical force applicator 50 comprises a force transducer 52 and a force probe 54. The force transducer 52 provides the static and oscillatory forces via the force probe 54. The force transducer 52 provides the oscillatory forces (F) when driven by an oscillatory electrical control signal and the static force when driven by a constant electrical control signal to the force probe 54. In further embodiments, the force transducer 52 provides the oscillatory forces (F) to the force probe 54 and the static force is provided by manually or electromechanically moving the force applicator carriage 350 which carries the mechanical force applicator 50, such as previously discussed above.

In further embodiments the mechanical force applicator 50 includes a layer of viscoelastic material placed between the force probe 54 and the skin overlying the bone, thereby supplementing the stiffness of the skin. The layer of viscoelastic material may be affixed to the force probe 54 on the face contacting the skin or may be a separate element loosely provided between the force probe 54 and the skin. Additionally, the viscoelastic material may be provided between the skin and the horizontal platform 140.

In various embodiments of a system for estimating the stiffness of a bone in vivo, the data analyzer 30 is communicatively coupled to the force transducer 52 and frequency response recorder 60 and the data analyzer 30 includes a storage medium and a processor. The storage medium contains computer readable and executable instructions for collecting the transmitted oscillatory forces as functions of time F(t) and oscillatory accelerations as functions of time a(t) of the skin-bone complex from the frequency response recorder. Additionally, the storage medium stores a parametric model of the skin-bone complex, such as was previously discussed above. The processor is provided for executing the instructions to transform a(t) and F(t) to functions of frequency, a(f) and F(f). The processor is also provided for executing the instructions to reduce a(f) and F(f) to accelerance frequency response data A(f) such as previously discussed. Further, the processor is provided for executing the instructions to determine a complex compliance frequency response function Y(f) and associated complex stiffness frequency response function H(f), to fit the parametric mathematical model to Y(f) to obtain a first set of parameters of the parametric mathematical model, including the stiffness of the bone ($k_b$), and to fit the parametric mathematical model to H(f) to obtain a second set of parameters of the parametric mathematical model, including the stiffness of the bone ($k_b$), such as previously discussed. Further, the processor determines the discrepancies between the first set of parameters and the second set of parameters as a measure of conformity thereof to the parametric mathematical model, such as previously discussed above.

In further embodiments of a system for estimating the stiffness of a bone in vivo, the processor is connected to a visual subsystem with a graphical user interface (GUI). The visual subsystem and graphical user interface provides information to the technician and/or operator of the system. In various embodiments, the information provided to the technician and/or operator includes displays of the fit of the parametric mathematical model to the accelerance frequency response function data A(f), the complex compliance frequency response function Y(f), and/or the complex stiffness frequency response function H(F). For example, graphical display of a curve representing experimental Y(f), H(f), and/or A(f) may be displayed with a curve generated by the best fit parameters overlaid in each instance. Additionally, statistical indicators of the fit of the parametric mathematical model to the accelerance frequency response function data A(f), the complex compliance frequency response function Y(f), and/or the complex stiffness frequency response function H(F) may be provided, such as in tabular form. For example, $R^2$ may be provided to indicate the goodness of the best fit parameters to the complex compliance frequency response function Y(f) and/or the complex stiffness frequency response function H(F).

Additionally, a method for determining the stiffness of a bone is provided. The method may be practiced using the system previously discussed. The method comprises applying a controlled superposition of static force and oscillatory force (F) measured as a first function of frequency F(f) spanning a range of frequencies to a skin-bone complex in vivo. The applied controlled oscillatory forces (F) thereby excite oscillatory accelerations (a) over the range of frequencies of the skin-bone complex. Then the resulting oscillatory accelerations (a) of the skin-bone complex are measured as a second function of frequency a(f). Further, as discussed in the previous method, F(f) and a(f) are transformed to obtain the stiffness of the skin-bone complex as a function of frequency H(f). Additionally, as previously discussed above, F(f) and a(f) are transformed to obtain the compliance of the skin-bone complex as a function of frequency Y(f). Then a parametric model is fit to H(f) to obtain a first set of parameters of the parametric model, including the stiffness of the bone $K_B$. Further, the parametric model is fit to Y(f) to obtain a second set of parameters of the parametric model, including the stiffness of the bone. As previously discussed above, discrepancies between the first set of parameters and the second set of parameters as a measure of conformity thereof to the parametric mathematical model are determined and are saved as a data set.

Further, in an effort to obtain an optimized data set, the static and oscillatory forces (F) are applied to a shifted region of the skin-bone complex and the oscillatory forces (F) and the resulting oscillatory accelerations (a) for the shifted region are measured. Further, as discussed in the previous method, F(f) and a(f) of the shifted region measurements are transformed to obtain the stiffness of the skin-bone complex as a function of frequency H(f). Additionally, as previously discussed above, F(f) and a(f) of the shifted region measurements are also transformed to obtain the compliance of the skin-bone complex as a function of frequency Y(f). Then the parametric model is fit to H(f) to obtain a new first set of parameters of the parametric model, including the stiffness of the bone, and the parametric model is also fit to Y(f) to obtain a new second set of parameters of the parametric model, including the stiffness of the bone. Repetition of collection of the oscillatory forces (F) and the resulting oscillatory accelerations (a) for shifted regions and analysis of the collected oscillatory forces (F) and oscillatory accelerations (a) to determine parameters of the parametric mathematical model is continued until the optimized data set is determined. Finally, the stiffness of the bone is determined from ($K_B$) values of the optimized data set as previously discussed above.

EXAMPLES

The following non-limiting examples illustrate the methods and/or systems of the present disclosure.

Example 1

System Validation on Artificial Human Ulna Bones

Experimental Protocol. The provided MRTA device in accordance with the previously described device for measuring the stiffness of the bone in vivo was validated by determining the accuracy of measurements of ulna flexural rigidity by MRTA, i.e., by the methods described herein, relative to measurements of ulna flexural rigidity and bending strength by QMT.

Ulna bending stiffness was non-destructively measured in ulnas by both MRTA and QMT. From ulna stiffness, flexural rigidity was determined using the aforementioned equation. Table 1 below summarizes the experimental design, including the methods of data collection, quantities measured and outcome.

TABLE 1

Experimental Design

| | Methods | |
| --- | --- | --- |
| | Dynamic MRTA 3-Point ending Tests | Quasi-Static Mechanical 3-Point Bending Tests |
| Measurements | Oscillatory Force Oscillatory Acceleration | Quasi-Static Force Quasi-Static Displacement |
| Outcomes | Bending Stiffness ($K_B$) Flexural Rigidity (EI) | Bending Stiffness ($K_B$) Flexural Rigidity (EI) |

Measurements were made on thirty-nine custom-made Sawbones® artificial human ulna bones (Vashon Island, Wash.). Because the artificial ulnas include a standard geometry (e.g., length of bone), calculation of EI to normalize transverse bending stiffness to account for individual variations in ulna length was not necessary. Nevertheless, EI was calculated for comparison to in vivo human data.

The ulnas were made with specific, incremental amounts of glass epoxy filling above and below the standard percentage distributed by Sawbones®. Since the glass filling represents cortical bone, the incremental differences in glass filling were expected to create a range of EI values. The ten different percentages of glass filling were: −10%, −7.5%, −5%, −2.5%, 0%, +2.5%, +5%, +6%, +7.5%, +10%. Where 0% indicates no change from the original (i.e., commercially distributed ulna) and the other percentages indicate various increases and decreases in glass filling compared to the standard.

QMT was used to non-destructively measure ulna bending stiffness. Ulnas were supported in the same orientation for MRTA and QMT stiffness tests. In QMT stiffness tests, repeated measurements of stiffness were collected until the internal coefficient of variation (standard deviation/mean) was less than or equal to 1.0% for five measurements taken consecutively.

Ulnas were positioned for MRTA stiffness measurements in position similar to QMT orientation for stiffness measurements. Specifically, the proximal end of the ulna was positioned on a secured humerus as it had been during QMT testing. Markings made on the tubercle of the coronoid process during QMT measurements were used to match the alignment of the MRTA measurements.

Data analysis was used to fit the 7-parameter model of the skin-bone complex to the raw data collected with MRTA.

Figure 7:
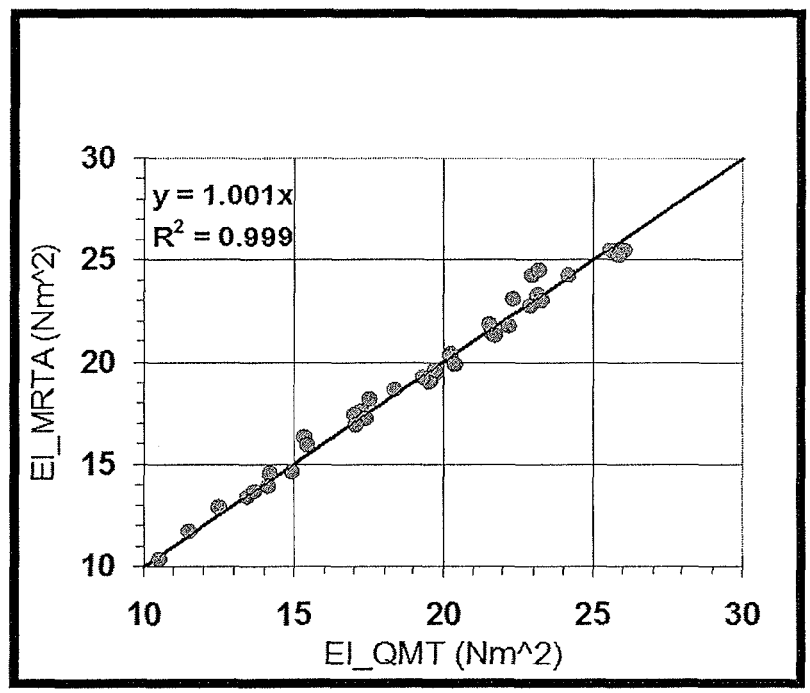
FIG. 7 depicts a regression analysis of MRTA and QMT measurements of flexural rigidity for artificial human ulnas.

Experimental Results. Referring to FIG. 7, it is shown that the flexural rigidity (EI) measured with MRTA corresponds very closely to those measured with QMT, which is the gold standard reference method.

Example 2

System Validation on Cadaveric Human Ulna Bones

Experimental Protocol. The provided MRTA device in accordance with the previously described device for measuring the stiffness of the bone in vivo was validated by determining the accuracy of measurements of ulna flexural rigidity of cadaveric human ulna bones by MRTA, i.e., by the methods described herein, relative to measurements of cadaveric human ulna flexural rigidity by QMT.

Ulna bending stiffness was non-destructively measured in human cadaveric ulnas by both MRTA and QMT. From ulna stiffness, flexural rigidity was determined using the aforementioned equation. Table 2 below summarizes the experimental design, including the methods of data collection, quantities measured and outcome.

TABLE 2

Experimental Design

| | Methods | |
| --- | --- | --- |
| | Dynamic MRTA 3-Point Bending Tests | Quasi-Static Mechanical 3-Point Bending Tests |
| Specimens | In situ cadaveric human ulnas Excised cadaveric human ulnas | Excised cadaveric human ulnas |

TABLE 2-continued

Experimental Design

| | Methods | |
| --- | --- | --- |
| | Dynamic MRTA 3-Point Bending Tests | Quasi-Static Mechanical 3-Point Bending Tests |
| Measurements | Oscillatory Force Oscillatory Acceleration | Quasi-Static Force Quasi-Static Displacement |
| Outcomes | Bending Stiffness ($K_B$) Flexural Rigidity (EI) | Bending Stiffness ($K_B$) Flexural Rigidity (EI) |

The test specimens used for this system validation consisted of 20 fresh-frozen cadaveric human arms. To maximize the likelihood that the tested specimens would exhibit a wide range of EI values, cadaveric human arms from twelve small women and eight large men of various ages (women=66-90 yrs, men=48-96 yrs) and body mass indices (BMI) (women=13.7-22.9 kg/m$^2$, men=25.0-39.7 kg/m$^2$) were acquired.

Cadaveric human ulnas with skin and soft tissues intact were positioned for MRTA stiffness measurements. Specifically, the humerous bone, with soft tissue excised, was secured in a vertical orientation and the ulna bone, with soft tissue intact, was positioned in a horizontal orientation with the distal end supported. Ulna EI in situ was then noninvasively measured by MRTA After collection of ulna EI in situ, the cadaveric human ulna was dissected to remove the hand, the radius distal to the radial tuberosity, and nearly all soft tissue (skin, fat, muscles, tendons, ligaments, vessels, nerves) from the arm. The elbow ligaments and the musculature immediately adjacent to the elbow capsule were left intact in order to maintain the natural positioning of the ulna in respect to the humerus during MRTA and QMT testing. The specimen was then set up for testing in the MRTA apparatus, and ulna EI was measured by MRTA in vitro. Specifically, the humerous bone, with soft tissue excised, was secured in a vertical orientation and the ulna bone, with soft tissue also excised, was positioned in a horizontal orientation with the distal end supported, wherein the humerous and ulna were connected by the intact elbow capsule.

QMT was used to non-destructively measure ulna bending stiffness in position similar to the MRTA orientation for stiffness measurements. Additionally, the ulnas were loaded at the same load point as in MRTA testing.

Data analysis was used to fit the 7-parameter model of the skin-bone complex to the raw data collected with MRTA.

Figure 8:
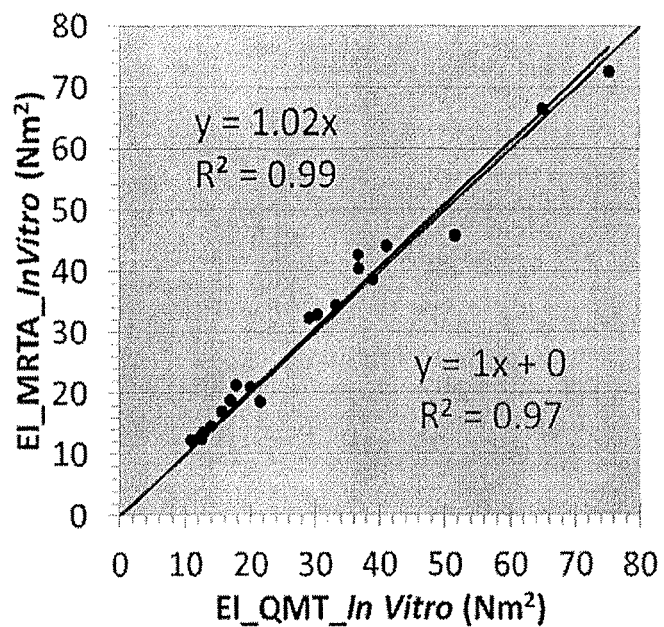
FIG. 8 depicts a regression analysis of MRTA and QMT measurements of flexural rigidity for in vitro cadaveric human ulnas.

Experimental Results. Referring to FIG. 8, it is shown that the flexural rigidity (EI) for the cadaveric human ulnas measures in vitro with MRTA corresponds very closely to those measured with QMT, which is the gold standard reference method. The upper regression line is the best fit of the data and the lower regression line represents the theoretical perfect agreement between MRTA and QMT with a slope of 1 and a y-intercept of 0.

Figure 9:
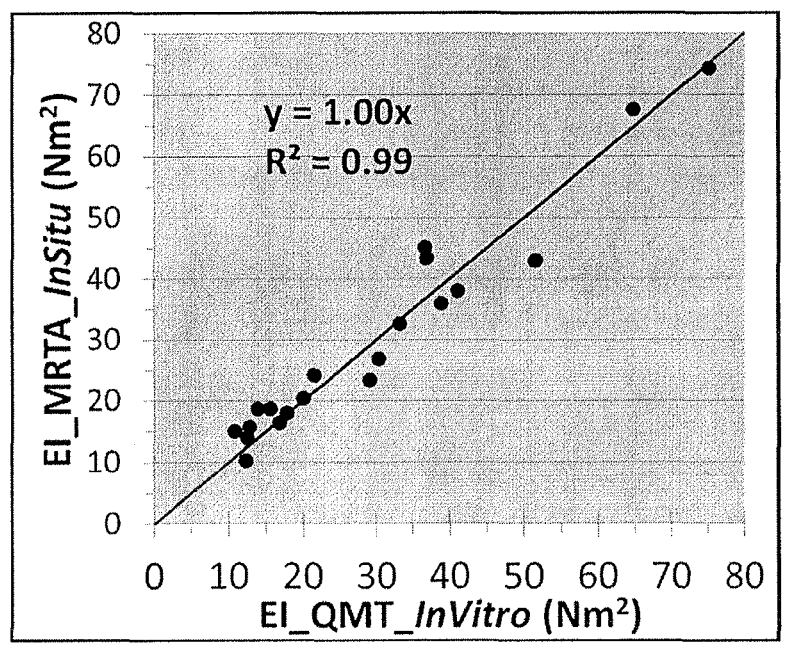
FIG. 9 depicts a corrected regression analysis of MRTA measurements of flexural rigidity for in situ cadaveric human ulnas and QMT measurements of flexural rigidity for in vitro cadaveric human ulnas.

Referring to FIG. 9, the EI values in situ consistently measured 24% higher than in vitro representing a fixed proportional error. The regression line shows that upon correcting the in situ measurements to be 24% lower, there is a high degree of agreement between the MRTA in situ measurements and the QMT in vitro measurements.

It should now be understood that various aspects of the disclosed invention are described herein and that such aspects may be utilized in conjunction with various other aspects.

In a first aspect, the disclosure provides a parametric model based computer implemented method for determining the stiffness of a bone. The method includes (1) applying a superposition of static and oscillatory forces (F) over a range of frequencies (f) to a region of a skin-bone complex thereby exciting oscillatory accelerations (a) over the range of frequencies (f) of the skin-bone complex; (2) receiving measurements of the oscillatory forces (F) as functions of time F(t) and the resulting oscillatory accelerations (a) as functions of time a(t) with a data receiver communicatively coupled to a controller including a processor and a storage medium containing computer readable and executable instructions; (3) repeating step (1)-(2), wherein the static and oscillatory forces (F) in step (1) are applied to a shifted region of the skin-bone complex; (4) repeating step (3) until an optimized data set is determined; and (5) determining the stiffness of the bone from ($K_B$) values of the optimized data set. When executed by the processor, the computer readable and executable instructions cause the controller to automatically: (i) transform a(t) and F(t) to functions of frequency, a(f) and F(f), (ii) reduce a(f) and F(f) to accelerance frequency response function data A(f), (iii) determine, a complex compliance frequency response function, Y(f) and associated complex stiffness frequency response function H(f), (iv) fit a parametric mathematical model to Y(f) to obtain a first set of parameters of the parametric mathematical model, including the stiffness of the bone ($K_B$), (v) fit the parametric mathematical model to H(f) to obtain a second set of parameters of the parametric mathematical model, including the stiffness of the bone ($K_B$), (vi) determine discrepancies between the first set of parameters and the second set of parameters as a measure of conformity thereof to the parametric mathematical model, and (vii) save the measure of conformity, the first set of parameters, and the second set of parameters as a data set.

In a second aspect, the disclosure provides a method of the first aspect, in which the complex compliance frequency response function Y(f) is determined by integrating A(f) twice and in which Y(f) is inverted to obtain the complex stiffness frequency response function H(f).

In a third aspect, the disclosure provides a method of any of the first or the second aspect, in which the data set further includes a record of at least one of Y(f) and H(f).

In a fourth aspect, the disclosure provides a method of any of the first to the third aspects, in which the measure of conformity between the first set of parameters and the second set of parameters is quantified in step (vi) as a root mean square therebetween of the percentage differences between each of the parameters of the first set of parameters and the second set of parameters.

In a fifth aspect, the disclosure provides a method of any of the first to the fourth aspects, in which the oscillatory forces (F) are applied to the skin-bone complex through an excitation frequency range having a minimum frequency of approximately 40 Hz and a maximum frequency of approximately 1200 Hz.

In a sixth aspect, the disclosure provides a method of any of the first to the fifth aspects, in which the parametric mathematical model is fit to Y(f) and H(f) in steps (iv)-(v) at a plurality of subranges within the excitation frequency range; a root mean square of the percentage differences between each of the parameters of the first set of parameters and the second set of parameters is quantified with the processor, for each of the plurality of subranges within the excitation frequency range; and a minimum resultant of the root mean square for the plurality of subranges is used as the measure of conformity in step (vi).

In a seventh aspect, the disclosure provides a method of the sixth aspect, in which the plurality of subranges within the excitation frequency range are generated by increasing the minimum frequency in approximately 5 Hz intervals and reducing the maximum frequency in approximately 25 Hz intervals.

In an eighth aspect, the disclosure provides a method of any of the sixth or seventh aspects, in which the minimum frequency is increased in approximately 5 Hz intervals until reaching approximately 180 Hz and the maximum frequency is reduced in approximately 25 Hz intervals until reaching approximately 700 Hz.

In a ninth aspect, the disclosure provides a method of any of the sixth to the eighth aspects, in which the minimum frequency is increased until reaching a resonant frequency representing a bone peak and the maximum frequency is decreased until reaching a resonant frequency representing a skin peak.

In a tenth aspect, the disclosure provides a method of any of the first to the ninth aspects, in which the stiffness of the bone determined in step (5) is the bending stiffness of the bone.

In an eleventh aspect, the disclosure provides a method of any of the first to the tenth aspects, in which step (3) further includes adjusting the static force in step (1).

In a twelfth aspect, the disclosure provides a method of any of the first to the eleventh aspects, in which step three further includes applying one or more layers of a viscoelestic material over the skin-bone complex, applying one or more layers of a viscoelestic material under the skin-bone complex, or applying one or more layers of a viscoelestic material over and under the skin-bone complex.

In a thirteenth aspect, the disclosure provides a method of any of the first to the twelfth aspects, in which the parametric mathematical model includes seven parameters including mass of the skin ($M_S$), transverse bending stiffness of the skin ($K_S$), damping coefficient of the skin ($B_S$) mass of the bone ($M_B$), transverse bending stiffness of the bone ($K_B$), damping coefficient of the bone ($B_B$), and damping coefficient of the surrounding soft tissue ($B_P$).

In a fourteenth aspect, the disclosure provides a method of the thirteenth aspect, in which the parametric mathematical model is fit to Y(f) and H(f) in steps (iv)-(v) at a plurality of subranges within the excitation frequency range; a root mean square of the percentage differences between each of the parameters of the first set of parameters and the second set of parameters is quantified with the processor, for each of the plurality of subranges within the excitation frequency range; and a minimum resultant of the root mean square for the plurality of subranges is used as the measure of conformity in step (vi).

In a fifteenth aspect, the disclosure provides a method of any of the first to the fourteenth aspects, in which the bone is a human ulna.

In a sixteenth aspect, the disclosure provides a method of any of the first to the fifteenth aspects, in which the stiffness of the bone from ($K_B$) values of the optimized data set is determined by selecting ($K_B$) from the first set of parameters, ($K_B$) from the second set of parameters, an average of ($K_B$) from the first set of parameters and ($K_B$) from the second set of parameters, or a weighted average of ($K_B$) from the first set of parameters and ($K_B$) from the second set of parameters of the optimized data set.

In a seventeenth aspect, the disclosure provides a system for estimating the stiffness of a bone in vivo. The system includes a device for measuring the stiffness of the bone in vivo and a data analyzer. The device for measuring the stiffness of the bone in vivo includes a bone positioning support, a mechanical force applicator, and a frequency response recorder, in which the bone positioning support is configured to position and support a skin-bone complex in an orientation and position for measurement. The mechanical force applicator includes an force transducer and a force probe and is configured to apply a superposition of static and oscillatory forces (F) over a range of frequencies (f) to a region of the skin-bone complex, wherein the oscillatory forces (F) excite oscillatory accelerations (a) of the skin-bone complex. The frequency response recorder is configured to measure and transmit to the data analyzer the oscillatory forces as functions of time F(t) and the oscillatory accelerations as functions of time a(t). The data analyzer is communicatively coupled to the force transducer and frequency response recorder. The data analyzer includes a storage medium containing computer readable and executable instructions for collecting the transmitted oscillatory forces as functions of time F(t) and oscillatory accelerations as functions of time a(t) of the skin-bone complex, the storage medium storing a parametric mathematical model of the skin-bone complex. The data analyzer also includes a processor for executing the instructions to transform a(t) and F(t) to functions of frequency, a(f) and F(f), to reduce a(f) and F(f) to accelerance frequency response data A(f), to determine a complex compliance frequency response function Y(f) and associated complex stiffness frequency response function H(f), to fit the parametric mathematical model to Y(f) to obtain a first set of parameters of the parametric mathematical model, including the stiffness of the bone ($K_B$), to fit the parametric mathematical model to H(f) to obtain a second set of parameters of the parametric mathematical model, including the stiffness of the bone ($K_B$), and to determine the discrepancies between the first set of parameters and the second set of parameters as a measure of conformity thereof to the parametric mathematical model.

In an eighteenth aspect, the disclosure provides a system of the seventeenth aspect, in which the complex compliance frequency response function Y(f) is determined by integrating A(f) twice and in which Y(f) is inverted to obtain the complex stiffness frequency response function H(f).

In a nineteenth aspect, the disclosure provides a system of any of the seventeenth to the eighteenth aspects, in which the measure of conformity between the first set of parameters and the second set of parameters is quantified as a root mean square therebetween of the percentage differences between each of the parameters of the first set of parameters and the second set of parameters.

In a twentieth aspect, the disclosure provides a system of any of the seventeenth to the nineteenth aspects, in which the parametric model of the skin-bone complex includes seven parameters including mass of the skin ($M_S$), transverse bending stiffness of the skin ($K_S$), damping coefficient of the skin ($B_S$) mass of the bone ($M_B$), transverse bending stiffness of the bone ($K_B$), damping coefficient of the bone ($B_B$), and damping coefficient of surrounding soft tissue ($B_P$).

In a twenty-first aspect, the disclosure provides a system of any of the seventeenth to the twentieth aspects, in which the oscillatory forces (F) are applied to the skin-bone complex through an excitation frequency range having a minimum frequency of approximately 40 Hz and a maximum frequency of approximately 1200 Hz.

In a twenty-second aspect, the disclosure provides a system of any of the seventeenth to the twenty-first aspects, in which the parametric mathematical model is repeatedly fit to Y(f) and H(f) at a plurality of subranges within the excitation frequency range; a root mean square of the percentage differences between each of the parameters of the first set of parameters and the second set of parameters is quantified with the algorithm processor, for each of the plurality of subranges within the sweeping frequency range; and a minimum resultant of the root mean square for the plurality of subranges is used as the measure of conformity.

In a twenty-third aspect, the disclosure provides a system of the twenty-second aspect, in which the plurality of subranges within the excitation frequency range are generated by increasing the minimum frequency in approximately 1 to 10 Hz intervals and reducing the maximum frequency in approximately 1 to 40 Hz intervals.

In a twenty-fourth aspect, the disclosure provides a system of any of the twenty-second or the twenty-third aspects, in which the minimum frequency is increased in approximately 5 Hz intervals until reaching approximately 180 Hz and the maximum frequency is decreased in approximately 25 Hz intervals until reaching approximately 700 Hz.

In a twenty-fifth aspect, the disclosure provides a system of any of the twenty-second to the twenty-fourth aspects, in which the minimum frequency is increased until reaching a resonant frequency representing a bone peak and the maximum frequency is decreased until reaching a resonant frequency representing a skin peak.

In a twenty-sixth aspect, the disclosure provides a system of any of the seventeenth to the twenty-fifth aspects, in which the bone is a human ulna.

In a twenty-seventh aspect, the disclosure provides a system of any of the seventeenth to the twenty-sixth aspects, in which the bone positioning support includes a platform configured to support a distal end of a human forearm, wherein the platform includes a layer of viscoelestic material thereon to dampen extraneous vibrations from the device.

In a twenty-eighth aspect, the disclosure provides a system of the twenty-seventh aspect, in which the bone positioning support further includes a bone positioning harness configured to support the proximal end of the human forearm.

In a twenty-ninth aspect, the disclosure provides a system of any of the seventeenth to the twenty-eighth aspects, in which the mechanical force applicator includes a layer of viscoelestic material placed between the force probe and the skin overlying the bone, thereby supplementing the stiffness of the skin.

In a thirtieth aspect, the disclosure provides a method for determining the stiffness of a bone. The method includes (1) applying a controlled superposition of static and oscillatory forces (F) measured as a first function of frequency F(f) over a range of frequencies to a skin-bone complex in vivo, thereby exciting oscillatory accelerations (a) over the range of frequencies of the skin-bone complex; (2) measuring the resulting oscillatory accelerations (a) of the skin-bone complex as a second function of frequency a(f); (3) transforming F(f) and a(f) to obtain the stiffness of the skin-bone complex as a function of frequency H(f); (4) transforming F(f) and a(f) to obtain the compliance of the skin-bone complex as a function of frequency Y(f); (5) fitting a parametric model to H(f) to obtain a first set of parameters of the parametric model, including the stiffness of the bone ($K_B$); (6) fitting the parametric model to Y(f) to obtain a second set of parameters of the parametric model, including the stiffness of the bone ($K_B$); (7) determining discrepancies between the first set of parameters and the second set of parameters as a measure of conformity thereof to the parametric mathematical model; (8) saving the measure of conformity, the first set of parameters, and the second set of parameters as a data set;

(9) repeating steps (1)-(8), wherein the static and oscillatory forces (F) in step (1) are applied to a shifted region of the skin-bone complex; (10) repeating step (9) until an optimized data set is determined; and (11) determining the stiffness of the bone from ($K_b$) values of the optimized data set.

In a thirty-first aspect, the disclosure provides a method of the thirtieth aspect, in which the measure of conformity between the first set of parameters and the second set of parameters is quantified in step (7) as a root mean square therebetween of the percentage differences between each of the parameters of the first set of parameters and the second set of parameters.

In a thirty-second aspect, the disclosure provides a method of any of the thirtieth or thirty-first aspects, in which the oscillatory forces (F) are applied to the skin-bone complex through an excitation frequency range having a minimum frequency of approximately 40 Hz and a maximum frequency of approximately 1200 Hz.

In a thirty-third aspect, the disclosure provides a method of any of the thirtieth to thirty-second aspects, in which the parametric mathematical model is fit to Y(f) and H(f) in steps (5)-(6) at a plurality of subranges within the excitation frequency range; a root mean square of the percentage differences between each of the parameters of the first set of parameters and the second set of parameters is quantified for each of the plurality of subranges within the sweeping frequency range; and a minimum resultant of the root mean square for the plurality of subranges is used as the measure of conformity in step (8).

In a thirty-fourth aspect, the disclosure provides a method of the thirty-third aspect, in which the plurality of subranges within the excitation frequency range are generated by increasing the minimum frequency in approximately 5 Hz intervals and reducing the maximum frequency in approximately 25 Hz intervals.

In a thirty-fifth aspect, the disclosure provides a method of any of the thirty-third or the thirty-fourth aspects, in which the minimum frequency is increased in approximately 5 Hz intervals until reaching approximately 180 Hz and the maximum frequency is reduced in approximately 25 Hz intervals until reaching approximately 700 Hz.

In a thirty-sixth aspect, the disclosure provides a method of any of the thirty-third to the thirty-fifth aspects, in which the minimum frequency is increased until reaching a resonant frequency representing a bone peak and the maximum frequency is decreased until reaching a resonant frequency representing a skin peak.

In a thirty-seventh aspect, the disclosure provides a method of any of the thirtieth to the thirty-sixth aspects, in which the parametric mathematical model includes seven parameters including mass of the skin ($M_S$), transverse bending stiffness of the skin ($K_S$), damping coefficient of the skin ($B_S$) mass of the bone ($M_B$), transverse bending stiffness of the bone ($K_B$), damping coefficient of the bone ($B_B$), and damping coefficient of the surrounding soft tissue ($B_P$).

In a thirty-eighth aspect, the disclosure provides a method of any of the thirty-fifth to the thirty-seventh aspects, in which the parametric mathematical model is fit to Y(f) and H(f) in steps (5)-(6) at a plurality of subranges within the excitation frequency range; a root mean square of the percentage differences between each of the parameters of the first set of parameters and the second set of parameters is quantified, for each of the plurality of subranges within the sweeping frequency range; and a minimum resultant of the root mean square for the plurality of subranges is used as the measure of conformity in step (8).

In a thirty-ninth aspect, the disclosure provides a method of any of the thirtieth to the thirty-eighth aspects, in which the bone is a human ulna.

In a fortieth aspect, the disclosure provides a method of any of the thirtieth to the thirty-ninth aspects, in which the data set further includes a record of at least one of Y(f) and H(f).

Having shown and described various embodiments in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

As will be evident from the foregoing disclosure, the methods of the invention are carried out non-invasively. As will be evident from the foregoing disclosure, the methods of the invention are carried out non-invasively. Additionally, the methods of the invention can be carried out by technicians without medical training and in the absence of medical supervision.

The invention claimed is:

1. A parametric model based computer implemented method for determining the stiffness of a bone, comprising:
   (1) applying a superposition of static and oscillatory forces (F) with a mechanical force applicator over a range of frequencies (f) to a region of a skin-bone complex thereby exciting oscillatory accelerations (a) over the range of frequencies (f) of the skin-bone complex;
   (2) receiving measurement data of the oscillatory forces (F as functions of time F(t) and obtaining the resulting oscillatory acceleration data (a) as functions of time a(t) with a data receiver communicatively coupled to a controller comprising a processor and a storage medium containing computer readable and executable instructions which, when executed by the processor, cause the controller to automatically:
      (i) transform a(t) and F(t) to functions of frequency, a(f) and F(f),
      (ii) reduce a(f) and F(f) to accelerance frequency response function data A(f),
      (iii) determine, a complex compliance frequency response function, Y(f) and associated complex stiffness frequency response function H(f),
      (iv) fit a parametric mathematical model to Y(f) to obtain a first set of parameters of the parametric mathematical model, including the stiffness of the bone ($K_B$),
      (v) fit the parametric mathematical model to H(f) to obtain a second set of parameters of the parametric mathematical model, including the stiffness of the bone ($K_B$),
      (vi) after fitting, determine discrepancies between each parameter of the first set of parameters and each corresponding parameter of the second set of parameters as a measure of conformity thereof to the parametric mathematical model, and (vii) save the measure of conformity, the first set of parameters, and the second set of parameters as a parameter set for the measured region of the skin-bone complex;

(3) positioning the mechanical force applicator at a laterally shifted region of the skin-bone complex and repeating steps (1)-(2), such that the static and oscillatory forces (F) in step (1) are applied to the laterally shifted region of the skin-bone complex, thereby obtaining a parameter set for the laterally shifted region of the skin-bone complex;

(4) repeating step (3) until the measure of conformity worsens, and determining an optimized parameter set based on the measure of conformity; and (5) determining the stiffness of the bone from $(k_b)$ values of the optimized parameter set.

2. The method of claim 1, wherein the complex compliance frequency response function Y(f) is determined by integrating A(f) twice and wherein Y(f) is inverted to obtain the complex stiffness frequency response function H(f).

3. The method of claim 1, wherein the parameter set further comprises a record of at least one of Y(f) and H(f).

4. The method of claim 1, wherein the measure of conformity between the first set of parameters and the second set of parameters is quantified in step (vi) as a root mean square therebetween of the percentage differences between each of the parameters of the first set of parameters and the second set of parameters.

5. The method of claim 1, wherein the oscillatory forces (F) are applied to the skin-bone complex through an excitation frequency range having a minimum frequency of approximately 40 Hz and a maximum frequency of approximately 1200 Hz.

6. The method of claim 5, wherein
the parametric mathematical model is fit to Y(f) and H(f) in steps (iv)-(v) at a plurality of subranges within the excitation frequency range;
a root mean square of the percentage differences between each of the parameters of the first set of parameters and the second set of parameters is quantified with the processor, for each of the plurality of subranges within the excitation frequency range; and
a minimum resultant of the root mean square for the plurality of subranges is used as the measure of conformity in step (vi).

7. The method of claim 6, wherein the plurality of subranges within the excitation frequency range are generated by increasing the minimum frequency in approximately 5 Hz intervals and reducing the maximum frequency in approximately 25 Hz intervals.

8. The method of claim 7, wherein the minimum frequency is increased in approximately 5 Hz intervals until reaching approximately 180 Hz and the maximum frequency is reduced in approximately 25 Hz intervals until reaching approximately 700 Hz.

9. The method of claim 6, wherein the minimum frequency is increased until reaching a resonant frequency representing a bone peak and the maximum frequency is decreased until reaching a resonant frequency representing a skin peak.

10. The method of claim 1, wherein the stiffness of the bone determined in step (5) is the bending stiffness of the bone.

11. The method of claim 1, wherein step (3) further comprises adjusting the static force in step (1).

12. The method of claim 1, wherein step (3) further comprises applying one or more layers of a viscoelestic material over the skin-bone complex, applying one or more layers of a viscoelestic material under the skin-bone complex, or applying one or more layers of a viscoelestic material over and under the skin-bone complex.

13. The method of claim 1, wherein the parametric mathematical model includes seven parameters comprising mass of the skin $(M_S)$, transverse bending stiffness of the skin $(K_S)$, damping coefficient of the skin $(B_S)$ mass of the bone $(M_B)$, transverse bending stiffness of the bone $(K_B)$, damping coefficient of the bone $(B_B)$, and damping coefficient of the surrounding soft tissue $(B_P)$.

14. The method of claim 13, wherein
the parametric mathematical model is fit to Y(f) and H(f) in steps (iv)-(v) at a plurality of subranges within the excitation frequency range;
a root mean square of the percentage differences between each of the parameters of the first set of parameters and the second set of parameters is quantified with the processor, for each of the plurality of subranges within the excitation frequency range; and
a minimum resultant of the root mean square for the plurality of subranges is used as the measure of conformity in step (vi).

15. The method of claim 14, wherein the bone is a human ulna.

16. The method of claim 1, wherein the stiffness of the bone from $(K_B)$ values of the optimized parameter set is determined by selecting $(K_B)$ from the first set of parameters, $(K_B)$ from the second set of parameters, an average of $(K_B)$ from the first set of parameters and $(K_B)$ from the second set of parameters, or a weighted average of $(K_B)$ from the first set of parameters and $(K_B)$ from the second set of parameters.

17. A method for determining the stiffness of a bone, comprising:

(1) applying a controlled superposition of static and oscillatory forces (F) measured as a first function of frequency F(f) over a range of frequencies to a skin-bone complex in vivo with a mechanical force applicator, thereby exciting oscillatory accelerations (a) over the range of frequencies of the skin-bone complex;

(2) measuring the resulting oscillatory accelerations (a) of the skin-bone complex as a second function of frequency a(f);

(3) transforming F(f) and a(f) to obtain the stiffness of the skin-bone complex as a function of frequency H(f);

(4) transforming F(f) and a(f) to obtain the compliance of the skin-bone complex as a function of frequency Y(f);

(5) fitting a parametric model to H(f) to obtain a first set of parameters of the parametric model, including the stiffness of the bone $(K_B)$;

(6) fitting the parametric model to Y(f) to obtain a second set of parameters of the parametric model, including the stiffness of the bone $(K_B)$;

(7) after fitting, determining discrepancies between each parameter of the first set of parameters and each corresponding parameter of the second set of parameters as a measure of conformity thereof to the parametric mathematical model;

(8) saving the measure of conformity, the first set of parameters, and the second set of parameters as a parameter set for the measured region of the skin-bone complex;

(9) positioning the mechanical force applicator at a laterally shifted region of the skin-bone complex and repeating steps (1)-(8), such that the static and oscillatory forces (F) in step (1) are applied to the laterally shifted region of the skin-bone complex, thereby obtaining a parameter set for the laterally shifted region of the skin-bone complex;

(10) repeating step (9) until the measure of conformity worsens, and determining an optimized parameter set based on the measure of conformity; and

(11) determining the stiffness of the bone from ($K_B$) values of the optimized parameter set.

18. The method of claim 17, wherein the measure of conformity between the first set of parameters and the second set of parameters is quantified in step (7) as a root mean square therebetween of the percentage differences between each of the parameters of the first set of parameters and the second set of parameters.

19. The method of claim 17, wherein the oscillatory forces (F) are applied to the skin-bone complex through an excitation frequency range having a minimum frequency of approximately 40 Hz and a maximum frequency of approximately 1200 Hz.

20. The method of claim 19, wherein
the parametric mathematical model is fit to Y(f) and H(f) in steps (5)-(6) at a plurality of subranges within the excitation frequency range;
a root mean square of the percentage differences between each of the parameters of the first set of parameters and the second set of parameters is quantified for each of the plurality of subranges within the excitation frequency range; and
a minimum resultant of the root mean square for the plurality of subranges is used as the measure of conformity in step (8).

21. The method of claim 20, wherein the plurality of subranges within the excitation frequency range are generated by increasing the minimum frequency in approximately 5 Hz intervals and reducing the maximum frequency in approximately 25Hz intervals.

22. The method of claim 21, wherein the minimum frequency is increased in approximately 5Hz intervals until reaching approximately 180Hz and the maximum frequency is reduced in approximately 25Hz intervals until reaching approximately 700Hz.

23. The method of claim 21, wherein the minimum frequency is increased until reaching a resonant frequency representing a bone peak and the maximum frequency is decreased until reaching a resonant frequency representing a skin peak.

24. The method of claim 17, wherein the parametric mathematical model includes seven parameters comprising mass of the skin ($M_S$), transverse bending stiffness of the skin ($K_S$), damping coefficient of the skin ($B_S$) mass of the bone ($M_B$), transverse bending stiffness of the bone ($K_B$), damping coefficient of the bone ($B_B$), and damping coefficient of the surrounding soft tissue ($B_P$).

25. The method of claim 22, wherein:
the parametric mathematical model is fit to Y(f) and H(f) in steps (5)-(6) at a plurality of subranges within the excitation frequency range;
a root mean square of the percentage differences between each of the parameters of the first set of parameters and the second set of parameters is quantified, for each of the plurality of subranges within the excitation frequency range; and
a minimum resultant of the root mean square for the plurality of subranges is used as the measure of conformity in step (8).

26. The method of claim 25, wherein the bone is a human ulna.

27. The method of claim 17, wherein the parameter set further comprises a record of at least one of Y(f) and H(f).

28. A parametric model based computer implemented method for determining the stiffness of a bone, comprising:
(1) applying a superposition of static and oscillatory forces (F) with a mechanical force applicator over a range of frequencies (f) to a region of a skin-bone complex thereby exciting oscillatory accelerations (a) over the range of frequencies (f) of the skin-bone complex;
(2) receiving measurement data of the oscillatory forces (F as functions of time F(t) and obtaining the resulting oscillatory acceleration data (a) as functions of time a(t) with a data receiver communicatively coupled to a controller comprising a processor and a storage medium containing computer readable and executable instructions which, when executed by the processor, cause the controller to automatically:
(i) transform a(t) and F(t) to functions of frequency, a(f) and F(f),
(ii) reduce a(f) and F(f) to accelerance frequency response function data A(f),
(iii) determine, a complex compliance frequency response function, Y(f) and associated complex stiffness frequency response function H(f),
(iv) fit a parametric mathematical model to Y(f) to obtain a first set of parameters of the parametric mathematical model, including the stiffness of the bone ($K_B$),
(v) fit the parametric mathematical model to H(f) to obtain a second set of parameters of the parametric mathematical model, including the stiffness of the bone ($K_B$),
(vi) after fitting, determine discrepancies between each parameter of the first set of parameters and each corresponding parameter of the second set of parameters as a measure of conformity thereof to the parametric mathematical model, wherein the measure of conformity between the first set of parameters and the second set of parameters is quantified as a root mean square therebetween of the percentage differences between each of the parameters of the first set of parameters and the second set of parameters, and
(vii) save the measure of conformity, the first set of parameters, and the second set of parameters as a parameter set for the measured region of the skin-bone complex;
(3) positioning the mechanical force applicator at a laterally shifted region of the skin-bone complex and repeating steps (1)-(2), such that the static and oscillatory forces (F) in step (1) are applied to the laterally shifted region of the skin-bone complex, thereby obtaining a parameter set for the laterally shifted region of the skin-bone complex;
(4) repeating step (3) until the measure of conformity worsens, and determining a optimized parameter set based on the measure of conformity; and
(5) determining the stiffness of the bone from ($k_b$) values of the optimized parameter set.

* * * * *

UNITED STATES PATENT AND TRADEMARK OFFICE
CERTIFICATE OF CORRECTION

PATENT NO.         : 10,299,719 B2                                     Page 1 of 1
APPLICATION NO.    : 14/782712
DATED              : May 28, 2019
INVENTOR(S)        : Lyn Bowman et al.

It is certified that error appears in the above-identified patent and that said Letters Patent is hereby corrected as shown below:

In the Specification

In Column 2, Line 35, delete "DxA" and insert --DXA--, therefor.

Signed and Sealed this
Twenty-seventh Day of August, 2019

Andrei Iancu
*Director of the United States Patent and Trademark Office*